United States Patent [19]
Soto-Jara et al.

[11] Patent Number: 5,948,763
[45] Date of Patent: *Sep. 7, 1999

[54] PEPTIDES AND PHARMACEUTICAL COMPOSITIONS THEREOF FOR TREATMENT OF DISORDERS OR DISEASES ASSOCIATED WITH ABNORMAL PROTEIN FOLDING INTO AMYLOID OR AMYLOID-LIKE DEPOSITS

[75] Inventors: Claudio Soto-Jara, New York, N.Y.; Marc H. Baumann, Helsinski, Finland; Blas Frangione, New York, N.Y.

[73] Assignee: New York University, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/630,645

[22] Filed: Apr. 10, 1996

Related U.S. Application Data

[63] Continuation-in-part of application No. 08/478,326, Jun. 6, 1995.

[51] Int. Cl.$^6$ .................................................. A61K 38/00
[52] U.S. Cl. ............................... 514/14; 514/15; 514/16; 514/17; 514/18
[58] Field of Search .................... 514/2, 14, 15, 514/16, 17, 18; 530/300, 326, 327, 328, 329, 330, 331

[56] References Cited

FOREIGN PATENT DOCUMENTS

WO 96/28471  9/1996  WIPO .
WO 97/21728  6/1997  WIPO .

OTHER PUBLICATIONS

Hilbich et al, J. Mol. Biol., 228:460–473, 1992.
Wille et al, Ciba Foundation Symposium 199, pp. 181–201, 1996.
Wood et al, Biochemistry, 34(3):724–730, 1995.
Borman et al, Science Jun. 17, 1996, pp. 33–34.
Rudinger et al "Peptide Hormones" ed Parsons, J.A. University Park Press, Jun. 1976, p. 6.
Burgess et al, The Journal of Cell Biology, 111:2129–2138, 1990.
Lazar et al, Molecular and Cellular Biology, 8(3):1247–1252, 1988.
Chou et al, "Empirical Predictions of Protein Conformation", *Ann. Rev. Biochem*, 47:251–276 (1978).
Stephen Wood et al, Prolines and Amyloidgenicity in Fragments of the Alzheimers Peptide β/A4, Biochemistry, vol. 34, pp. 724–730, 1995.
Claudio Soto et al, Two Conformational States of Amyloid β–Peptide: Implications for the Pathogenesis of Alzheimer's Disease, Neuroscience Letters, vol. 186, pp. 115–118, 1995.
Claudio Soto et al, Structural Determinants of the Alzheimer's Amyloid β–Peptide Journal of Neurochemistry, vol. 63, pp. 1191–1198, 1994.
Claudio Soto et al, The α–Helical to β–Strand Transition in the Amino–Terminal Fragment of the Amyloid β–Peptide Modulates Amyloid Formation, Journal of Biochemistry, vol. 20, No. 7, pp. 3063–3067, 1995.

*Primary Examiner*—Patricia A. Duffy
*Attorney, Agent, or Firm*—Browdy and Neimark

[57] ABSTRACT

Novel peptides capable of interacting with a hydrophobic structural determinant on a protein or peptide for amyloid or amyloid-like deposit formation inhibit and structurally block the abnormal folding of proteins and peptides into amyloid or amyloid-like deposits. Methods for preventing, treating or detecting disorders or diseases associated with amyloid-like fibril deposits, such as Alzheimer's disease and prion-related encephalopathies, are also provided.

14 Claims, 16 Drawing Sheets

| PROTEIN | AMINO ACID SEQUENCE |
|---|---|
| ALZHEIMER'S β - AMYLOID | 16 K L V F F A̲ E̲ D 23 |
| AMYLOID A | 1 R S F F S F L G 8 |
| GELSOLIN AMYLOID | 187 D̲ C F I L D L G 194 |
| AMYLOID L | 18 R V T I T C Q A 25 |
| β2 - MICROGLOBULIN AMYLOID | 61 S F Y L L Y Y T 68 |
| APOLIPOPROTEIN A1 AMYLOID | 13 D L A T V Y V D 20 |

ANTI-AMYLOID 1      S R G D L P F F P V P I G D S
ANTI-AMYLOID 2      R D L P F F P V P I D
ANTI-AMYLOID 3      R D F I P L P L D
ANTI-AMYLOID 4      R D Y L P Y Y P L D

FIG. 6A
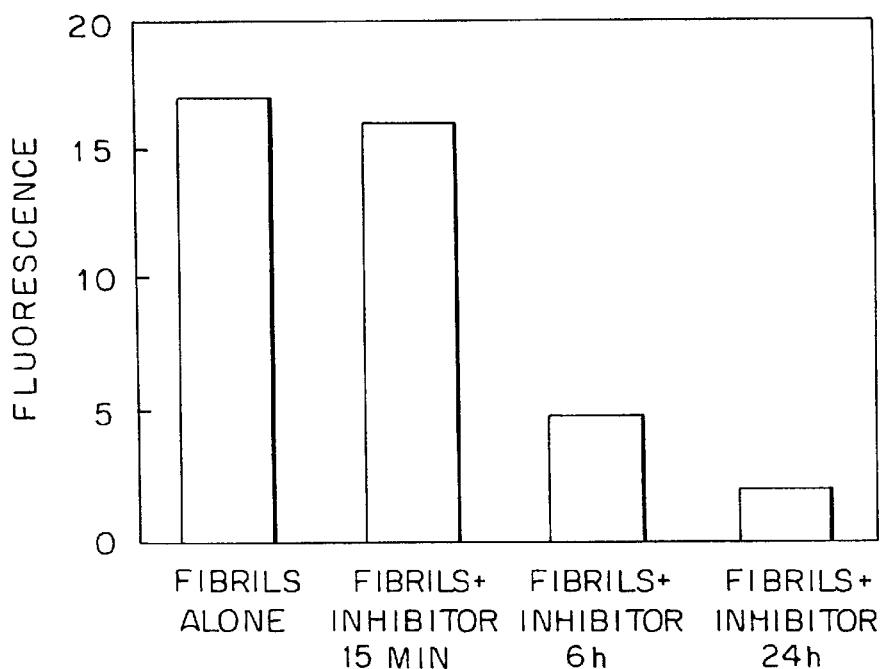
FIG. 7A
| PROTEIN | AMINO ACID SEQUENCE |
|---|---|
| AMPHOTERIN (HMG-1) | 10 G K M S S Y A F F V Q T C R E E H K 27 |
FIG. 7B
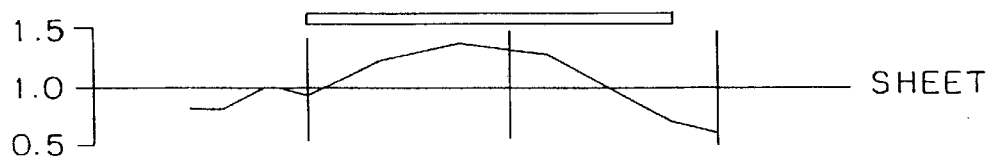

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Lys Leu Val Phe Phe Ala Glu Asp
    1               5

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Arg Ser Phe Phe Ser Phe Leu Gly
    1               5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Asp Cys Phe Ile Leu Asp Leu Gly
    1               5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Arg Val Thr Ile Thr Cys Gln Ala
    1               5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ser Phe Tyr Leu Leu Tyr Tyr Thr
1               5

(2) INFORMATION FOR SEQ ID NO:6:

(i) SEQUENCE CHARACTERISTICS:
　　　　(A) LENGTH: 8 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:6:

Asp Leu Ala Thr Val Tyr Val Asp
1               5

(2) INFORMATION FOR SEQ ID NO:7:

(i) SEQUENCE CHARACTERISTICS:
　　　　(A) LENGTH: 15 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:7:

Ser Arg Gly Asp Leu Pro Phe Phe Pro Val Pro Ile Gly Asp Ser
1               5                  10                  15

(2) INFORMATION FOR SEQ ID NO:8:

(i) SEQUENCE CHARACTERISTICS:
　　　　(A) LENGTH: 11 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:8:

Arg Asp Leu Pro Phe Phe Pro Val Pro Ile Asp
1               5                  10

(2) INFORMATION FOR SEQ ID NO:9:

(i) SEQUENCE CHARACTERISTICS:
　　　　(A) LENGTH: 9 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:9:

Arg Asp Phe Ile Pro Leu Pro Leu Asp
1               5

(2) INFORMATION FOR SEQ ID NO:10:

(i) SEQUENCE CHARACTERISTICS:
　　　　(A) LENGTH: 10 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:10:

Arg Asp Tyr Leu Pro Tyr Tyr Pro Leu Asp
        1               5                   10

(2) INFORMATION FOR SEQ ID NO:11:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Gly Lys Met Ser Ser Tyr Ala Phe Phe Val Gln Thr Cys Arg Glu Glu
        1               5                   10                  15

His Lys (2) INFORMATION FOR SEQ ID NO:12:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Phe Asn Asn Gly Asp Cys Phe Ile Leu Asp Leu Gly Asn Asn Ile
        1               5                   10                  15

(2) INFORMATION FOR SEQ ID NO:13:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Arg Ser Phe Phe Ser Phe Leu Gly Glu Ala Phe Asp Gly Ala Arg
        1               5                   10                  15

(2) INFORMATION FOR SEQ ID NO:14:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

Gln Lys Leu Val Phe Phe Ala Glu Asp Val Gly
        1               5                   10

(2) INFORMATION FOR SEQ ID NO:15:

(i) SEQUENCE CHARACTERISTICS:
            (A) LENGTH: 9 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO:15:

Arg Asp Leu Pro Phe Phe Pro Val Asp
    1               5

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Leu Pro Phe Phe Pro Val Asp
    1               5

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Leu Pro Phe Phe Val Asp
    1               5

(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Leu Pro Phe Phe Asp
    1               5

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Leu Pro Phe Phe
    1

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: single -continued

```
        (D) TOPOLOGY: linear (ii) MOLECULE TYPE: peptide (xi) SEQUENCE DESCRIPTION: SEQ ID NO:20:

Arg Asp Leu Pro Ile Val Pro Leu Pro Ile Asp
    1               5                   10

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Leu Pro Ile Val Pro Leu Asp
    1               5

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Leu Pro Ile Val Asp
    1               5

(2) INFORMATION FOR SEQ ID NO:23:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Gly Ala Ala Ala Ala Gly Ala Val Val Gly Gly Leu
    1               5                   10

(2) INFORMATION FOR SEQ ID NO:24:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Arg Asp Ala Pro Ala Ala Pro Val Val Pro Leu Asp
    1               5                   10

(2) INFORMATION FOR SEQ ID NO:25:

(i) SEQUENCE CHARACTERISTICS:
        (A) LENGTH: 7 amino acids
        (B) TYPE: amino acid
        (C) STRANDEDNESS: single
```

-continued (D) TOPOLOGY: linear (ii) MOLECULE TYPE: peptide (xi) SEQUENCE DESCRIPTION: SEQ ID NO:25:

Ala Ala Pro Val Val Pro Asp
    1               5

(2) INFORMATION FOR SEQ ID NO:26:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Val His Val Ser Glu Glu Gly Thr Glu Pro Glu Ala
    1               5                   10

PEPTIDES AND PHARMACEUTICAL COMPOSITIONS THEREOF FOR TREATMENT OF DISORDERS OR DISEASES ASSOCIATED WITH ABNORMAL PROTEIN FOLDING INTO AMYLOID OR AMYLOID-LIKE DEPOSITS

CROSS-REFERENCE TO RELATED APPLICATION

The present application is a continuation-in-part of U.S. application Ser. No. 08/478,326, filed Jun. 6, 1995, the entire contents of which are hereby incorporated by reference.

GOVERNMENT LICENSE RIGHTS

The U.S. Government has a paid-up license in this invention and the right in limited circumstances to require the patent owner to license others on reasonable terms as provided for by the terms of Grant No. 10953 awarded by National Institutes of Health.

BACKGROUND OF THE INVENTION

1. Field of the Invention

This invention relates to the field of therapeutic peptides for the prevention and treatment of disorders or diseases resulting from abnormal formation of amyloid or amyloid-like deposits, such as, but not limited to, prion-related encephalophathies, Alzheimer's dementia or disease (AD), and other amyloidosis disorders. This invention also relates to the use of the peptides in preventing the formation of or in promoting the redissolution of these insoluble amyloid or amyloid-like deposits.

2. Description of the Background Art

Alzheimer's disease (AD) is the most common form of dementia in adults (C. Soto et al. *J. Neurochem.* 63:1191–1198, 1994), constituting the fourth leading cause of death in the United States. Approximately 10% of the population over 65 years old is affected by this progressive degenerative disorder that is characterized by memory loss, confusion and a variety of cognitive disabilities. One of the key events in AD is the deposition of amyloid as insoluble fibrous masses (amyloidogenesis) resulting in extracellular neuritic plaques and deposits around the walls of cerebral blood vessels. The main component of amyloid is a 4.1–4.3 kDa hydrophobic peptide, named amyloid β-peptide (Aβ), that is codified in chromosome 21 as part of a much longer amyloid precursor protein APP (Muller-Hill and Beyreuther, *Ann. Rev. Biochem.* 38:287–307, 1989). The APP starts with a leader sequence (signal peptide), followed by a cysteine-rich region, an acidic-rich domain, a protease inhibitor motif, a putative N-glycosylated region, a transmembrane domain, and finally a small cytoplasmic region. The Aβ sequence begins close to the membrane on the extracellular side and ends within the membrane. Two-thirds of Aβ faces the extracellular space, and the other third is embedded in the membrane (Kang et al. *Nature* 325:503–507, 1987; Dyrks et al. *EMBO J.* 7:949–957, 1988). Several lines of evidence suggest that amyloid may play a central role in the early pathogenesis of AD.

Evidence that amyloid may play an important role in the early pathogenesis of AD comes primarily from studies of individuals affected by the familial form of AD (FAD) or by Down's syndrome. Down's syndrome patients have three copies of APP gene and develop AD neuropathology at an early age (Wisniewski et al., *Ann. Neurol.* 17:278–282, 1985). Genetic analysis of families with hereditary AD revealed mutations in chromosome 21, near or within the Aβ sequence (Forsell et al., *Neurosci. Lett.* 184:90–93, 1995). Moreover, recently it was reported that transgenic mice expressing high levels of human mutant APP progressively develop amyloidosis in brain (Games et al., *Nature* 373:523–527, 1995). These findings appear to implicate amyloidogenesis in the pathophysiology of AD.

Recently, the same peptide that forms amyloid deposits in AD brain was also found in a soluble form (sAβ) normally circulating in the human body fluids (Seubert et al., *Nature* 359:355–327, 1992; Shoji et al., *Science* 258:126–129, 1992). It is believed that the conversion of sAβ to insoluble fibrils is initiated by a conformational or proteolytic modification of the 2–3 amino acid longer soluble form. It has been suggested that the amyloid formation is a nucleation-dependent phenomena in which the initial insoluble "seed" allows the selective deposition of amyloid (Jarrett et al., *Biochem.* 32:4693–4697, 1993).

Peptides containing the sequence 1-40 or 1-42 of Aβ and shorter derivatives can form amyloid-like fibrils in the absence of other protein (Pike et al., *J. Neurosci.* 13:1676–1687, 1993), suggesting that the potential to form amyloid resides mainly in the structure of Aβ. The relation between the primary structure of Aβ and its ability to form amyloid-like fibrils was analyzed by altering the sequence of the peptide. Substitution of hydrophilic residues for hydrophobic ones in the internal Aβ hydrophobic regions (amino acids 17–21) impaired fibril formation (Lorenzo et al., *Proc. Natl. Acad. Sci. USA* 91:12243–12247, 1994), suggesting that Aβ assembly is partially driven by hydrophobic interactions. Indeed, larger Aβ peptides (Aβ1-42/43) comprising two or three additional hydrophobic C-terminal residues are more amyloidogenic (Soto et al., *J. Neurochem.* 63:1191–1198, 1994). Secondly, the conformation adopted by Aβ peptides is crucial in amyloid formation. Aβ incubated at different pH, concentrations and solvents has mainly an α-helical (random coil) or a β-sheet secondary structure (Hilbich et al., *J. Mol. Biol.* 228:460–473, 1992; Jarrett et al., *Biochem* 32:4693–4697, 1993; Barrow et al., *J. Mol. Biol.* 225:1075–1093, 1992). The Aβ peptide with α-helical or random coil structure aggregates slowly; Aβ with β-sheet conformation aggregates rapidly (Burdick et al., *J. Biol. Chem.* 267:546–554, 1992; Zagorski et al., *Biochem.* 31:5621–5631, 1992; Soto et al., *J. Biol. Chem.* 270:3063–3067, 1995). The importance of hydrophobicity and β-sheet secondary structure on amyloid formation also is suggested by comparison of the sequence of other amyloidogenic proteins.

Analysis of Aβ aggregation by turbidity measurements indicates that the length of the C-terminal domain of Aβ influences the rate of Aβ assembly by accelerating nucleus formation (Soto et al., 1994, supra; Soto et al, *Neurosci. Lett.* 186:115–118, 1995). Thus, the C-terminal domain of Aβ may regulate fibrillogenesis. However, in vitro modulators of Aβ amyloid formation such as metal cations (Zn, Al) (Soto et al., *Biochem. J.* 314:701–707, 1996; Jarrett et al., *Cell* 73:1055–058, 1993), heparan sulphate proteoglycans (Bush et al., *Science* 265:1464–1467, 1994) and apoliprotein E (Exley et al., *FEBS Lett.* 324:293–295, 1993) interact with the 12–28 region of Aβ. Moreover, mutations in the βPP gene within the N-terminal Aβ domain yield analogs more fibrillogenic (Soto et al., 1995, supra; Buee et al., *Brain Res.* 627:199–204, 1993; Strittmatter et al., *Proc. Natl. Acad. Science. (USA)* 90:1977–1981, 1993; Wisniewski et al., Biochem. Biophys. Res. Commun. 179:1247–1254, 1991). Finally, while the C-terminal domain of Aβ invariably adopts a β-strand structure in aqueous solutions, environmental parameters determine the existence of alternative conformation in the Aβ N-terminal domain (Hilbich et al., 1992, supra; Burdick et al., 1992, supra). Therefore, the N-terminus may be a potential target site for inhibition of the initial random coil to β-sheet conformational change.

The emerging picture from studies with synthetic peptides is that Aβ amyloid formation is dependent on hydrophobic interactions of Aβ peptides adopting an antiparallel β-sheet conformation and that both the N- and C-terminal domains are important for amyloid formation. The basic unit of fibril formation appears to be the conformer adopting an antiparallel β-sheet composed of strands involving the regions 10–24 and 29–40/42 of the peptide (Pike et al., 1993, supra; Clements et al., $Neurosci.\ Lett.$ 161:17–20, 1993). Amyloid formation proceeds by intermolecular interactions between the β-strands of several monomers to form an oligomeric β-sheet structure precursor of the fibrillar β-cross conformation. Wood et al., 1995, supra, reported the inserting of aggregation-blocking prolines into proteins and peptides to prevent aggregation without affecting the structure or function of the native protein. In this manner, the authors suggest that novel proteins can be designed to avoid the problem of aggregation as a barrier to their production.

To date there is no cure or treatment for AD and even the unequivocal diagnosis of AD can only be made after postmortem examination of brain tissues for the hallmark neurofibrillary tangles (NFT) and neuritic plaques. However, there are several recent publications outlining strategies for the treatment of Alzheimer's disease.

Heparin sulfate (glycosoaminoglycan) or the heparin sulfate proteoglycan, perlecan, has been identified as a component of all amyloids and has also been implicated in the earliest stages of inflammation-associated amyloid induction. Kisilevsky et al., $Nature\ Medicine$ 1(2):143–148, (1995) describes the use of low molecular weight (135–1,000 Da) anionic sulfonate or sulfate compounds that interfere with the interaction of heparin sulfate with the inflammation-associated amyloid precursor and the β-peptide of AD. Heparin sulfate specifically influences the soluble amyloid precursor (SAA2) to adopt an increased β-sheet structure characteristic of the protein-folding pattern of amyloids. These anionic sulfonate or sulfate compounds were shown to inhibit heparin-accelerated Alzheimer's Aβ fibril formation and were able to disassemble preformed fibrils in vitro as monitored by electron micrography. Moreover, when administered orally at relatively high concentrations (20 or 50 mM), these compounds substantially arrested murine splenic inflammation-associated amyloid progression in vivo in acute and chronic models. However, the most potent compound, poly-(vinylsulfonate), was acutely toxic.

Anthracycline 4'-iodo-4'-deoxy-doxorubicin (IDOX) has been observed clinically to induce amyloid resorption in patients with immunoglobin light chain amyloidosis (AL). Merlini et al., $Proc.\ Natl.\ Acad.\ Sci.\ USA$ 92:2959–2963 (1995), elucidated its mechanism of action. IDOX was found to bind strongly via hydrophobic interactions to two distinct binding sites (Scatchard analysis) in five different tested amyloid fibrils, inhibiting fibrillogenesis and the subsequent formation of amyloid deposits in vitro. Preincubation of IDOX with amyloid enhancing factor (AEF) also reduced the formation of amyloid deposits. Specific targeting of IDOX to amyloid deposits in vivo was confirmed in an acute murine model. This binding is distinct from heparin sulfate binding as removal of the glycosaminoglycans from extracted amyloid fibrils with heparinases did not modify IDOX binding. The common structural feature of all amyloids is a β-pleated sheet conformation. However, IDOX does not bind native amyloid precursor light chains which suggests that the β-pleated sheet backbone alone is not sufficient to form the optimal structure for IDOX binding, and that it is the fibril cross-β-sheet quaternary structure that is required for maximal IDOX binding. It has been found that the amount of IDOX extracted from spleens is correlated with amyloid load and not circulating serum precursor amyloid levels. IDOX, however, is also extremely toxic.

The regulation and processing of amyloid precursor protein (APP) via inhibition or modulation of phosphorylation of APP control proteins has also been investigated in U.S. Pat. No. 5,385,915 and WO 9427603. Modulating proteolytic processing of APP to nucleating forms of AD has also been examined in AU 9338358 and EP569777. WO 95046477 discloses synthetic peptides of composition X-X-N-X coupled to a carrier, where X is a cationic amino acid and N is a neutral amino acid, which inhibit Aβ binding to glycosoaminoglycan. Peptides containing Alzheimer's Aβ sequences that inhibit the coupling of β-1-antichymotrypsin and Aβ are disclosed in WO 9203474.

Abnormal protein folding is also widely believed to be the cause of prion-related encephalophathies, such as Creutzfeldt-Jakob disease (CJD) and Gerstmann-Straussler-Scheinker disease (GSS) in humans, scrapie in sheep and goats, and spongiform encephalopathy in cattle.

The cellular prion protein ($PrP^c$) is a sialoglycoprotein encoded by a gene that in humans is located on chromosome 20 (Oesch, B. et al., $Cell$ 40:735–746, (1985); Basler, K. et al., 46:417–428 (1986); Liao, Y. J. et al., $Science$ 233:364–367 (1986); Meyer, R. K. et al., $Proc.\ Natl.\ Acad.\ Sci.\ USA$ 83:2310–2314 (1986); Sparkes, R. S. et al., $Proc.\ Natl.\ Acad.\ Sci.\ USA$ 83:7358–7362 (1986); Bendheim, P. E. et al. $J.\ Infect.\ Dis.$ 158:1198–1208 (1988); Turk, E. et al. $Eur.\ J.\ Biochem.$ 176:21–30 (1988)). The PrP gene is expressed in neural and non-neural tissues, the highest concentration of mRNA being in neurons (Chesebro, B. et al., $Nature$ 315:331–333 (1985); Kretzschmar, H. A. et al., $Am.\ J.\ Pathol.$ 122:1–5 (1986); Brown, H. R. et al., $Acta\ Neuropathol.$ 80:1–6 (1990); Cashman, N. R. et al., $Cell$ 61:185–192 (1990); Bendheim, P. E., $Neurology$ 42:149–156 (1992)).

The translation product of PrP gene consists of 253 amino acids in humans (Kretzschmar, H. A. et al., $DNA$ 5:315–324 (1986); Pucket, C. et al., $Am.\ J.\ Hum.$ 49:320–329 (1991)), 254 in hamster and mice or 256 amino acids in sheep and undergoes several post-translational modifications. In hamsters, a signal peptide of 22 amino acids is cleaved at the N-terminus, 23 amino acids are removed from the C-terminus on addition of a glycosyl phosphatidylinositol (GPI) anchor, and asparagine-linked oligosaccharides are attached to residues 181 and 197 in a loop formed by a disulfide bond (Turk, E. et al., $Eur.\ J.\ Biochem.$ 176:21–30 (1988); Hope, J. et al., $EMBO\ J.$ 5:2591–2597 (1986); Stahl, N. et al., $Cell$ 51:229–240 (1987); Stahl, N. et al., $Biochemistry$ 29:5405–5412 (1990); Safar, J. et al., $Proc.\ Natl.\ Acad.\ Sci.\ USA$ 87:6377 (1990)).

In prion-related encephalopathies, $PrP^c$ is converted into an altered form designated $PrP^{Sc}$, that is distinguishable from $PrP^c$ in that $PrP^{Sc}$ (1) aggregates; (2) is proteinase K resistant in that only the N-terminal 67 amino acids are removed by proteinase K digestion under conditions in which $PrP^c$ is completely degraded; and (3) has an alteration in protein conformation from α-helical for $PrP^{Sc}$ to an altered form (Oesch B. et al., Cell 40:735–746 (1985); Bolton, D. C. et al., $Science$ 218:1309–1311 (1982);

McKinley, M. P. et al., *Cells* 35:57–62 (1982); Bolton, D. C. et al., *Biochemistry* 23:5898–5905 (1984); Prusiner, S. B. et al., *Cell* 38:127–134 (1984); Bolton, D. C. et al., *Arch. Biochem. Biophys.* 258:1515–22 (1987)).

Several lines of evidence suggest that $PrP^{Sc}$ may be a key component of the transmissible agent responsible for prion-related encephalopathies (Prusiner, S. B. *Science* 252:1515–22 (1991)) and it has been established that its protease-resistant core is the major structural protein of amyloid-like fibrils that accumulate intracerebrally in some of these conditions (Brendheim, P. E. et al., *Nature* 310:418–421 (1984); DeArmond, S. J. et al., *Cell* 41:221–235 (1985); Kitamoto, T. et al., *Ann. Neurol.* 20:204–208 (1986); Robert, G. W. et al., *N. Engl. Med.* 315:1231–1233 (1986); Ghetti, B. et al., *Neurology* 39:1453–1461 (1989); Tagliavini, F. et al., *EMBO J.* 10:513–519 (1991); Kitamoto, T. et al., *Neurology* 41:306–310 (1991)).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention relates to peptides capable of interacting or binding to a structural determinant on a protein or peptide for amyloid or amyloid-like deposit formation so as to inhibit or structurally block the abnormal folding of the protein or peptide into an amyloid or amyloid-like deposit, such as is observed in Alzheimer's disease, amyloidosis disorders, prion-related encephalophathies, etc. The peptide includes a hydrophobic cluster of at least three hydrophobic amino acid residues, similar to those of the protein or peptide with which they interact, where one of the hydrophobic residues is preferably a proline residue. The peptide according to the present invention may also include charged amino acids at one or both ends of the peptide.

One object of the present invention is to overcome the deficiencies of the prior art, including reducing the toxicity and side effects in comparison to compounds and therapeutic methods available in the prior art.

Another object of the present invention is to provide a peptide having a hydrophobic cluster of amino acids which blocks β-sheet formation between structural determinants on proteins or peptides that leads to the aggregation of abnormally folded proteins or peptides as amyloid or amyloid-like deposits.

A further object of the present invention is to provide pharmaceutical compositions and methods for the prevention or therapeutic treatment of disorders or diseases associated with abnormal protein folding into amyloid or amyloid-like deposits.

Still another object of the present invention is to provide a method for detecting disorders or diseases associated with amyloid or amyloid-like fibril deposits.

BRIEF DESCRIPTION OF THE DRAWINGS

FIG. 1A is the primary structure of the amyloidogenic sequence of peptides involved in the formation of several amyloid deposits. The sequences correspond to: amyloid β-peptide (SEQ ID NO: 1) found in Alzheimer's disease, its Dutch variant and Downs Syndrome; amyloid A (SEQ ID NO: 2) found in secondary amyloidosis and familial Mediterranean fever; gelsolin amyloid (SEQ ID NO: 3) related to familial amyloidosis of Finnish type; amyloid L (SEQ ID NO: 4) found in immunoglobulin-related primary amyloidosis; β2-microglobulin amyloid (SEQ ID NO: 5) found in patients with chronic hemodialysis-related amyloidosis; and apolipoprotein A1 amyloid (SEQ ID NO: 6) related to familial amyloidotic polyneuropathy. Amino acids written in bold correspond to hydrophobic residues and those underlined represent positions with mutation related to the hereditary form of the disease. FIG. 1B provides the β-sheet prediction for the 15 amino acid fragments containing the sequences shown in FIG. 1A. The solid bar represents regions with a high probability of adopting a β-sheet structure.

FIG. 2A shows the amino acid sequences four anti-amyloid peptides labeled as anti-amyloid 1 (SEQ ID NO: 7), anti-amyloid 2 (SEQ ID NO: 8), anti-amyloid 3 (SEQ ID NO: 9) and anti-amyloid 4 (SEQ ID NO: 10). Hydro-phobic amino acids are highlighted in bold. FIG. 2B shows the circular dichroism spectrum of the anti-amyloid peptide 1 (SEQ ID NO: 7) recorded as described in Example 1.

FIG. 4A shows the dose-dependent inhibition of amyloidogenesis, using anti-amyloid peptide 1 (shown as filled squares) and a 15 amino acid-non related peptide as a control (shown as unfilled square). The incubation time was 24 hours at room temperature and the Aβ concentration was 1 mg/ml in 0.1 M Tris, pH 7.4. FIG. 4B shows the effect of anti-amyloid peptide 1 (SEQ ID NO: 7) on the amyloid formation after various incubation times. The inhibitory effect of the peptide remained unaltered over several days of incubation. Incubations containing Aβ, alone, are depicted by unfilled squares; incubations of Aβ, and a control peptide are depicted by unfilled circles; and incubations of Aβ and anti-amyloid peptide 1 are depicted by filled squares. The Aβ concentration used was 1 mg/ml incubated in a molar ratio of anti-amyloid peptide 1 or control peptide of 1:20. Neither the anti-amyloid peptide 1 nor the control peptide gave fluorescence values over the background level of 1–2 fluorescence units.

FIGS. 6A–C show the effects of anti-amyloid peptide 1 on the redissolution of preformed fibrils. Amyloid fibrils were formed by incubating Aβ (1 mg/ml) for 3 days at room temperature. Anti-amyloid peptide 1 was then added in a molar ratio 1:50 (Aβ:anti-amyloid peptide 1). The incubation was continued for 15 minutes, 6 hours or 24 hours and the amyloid formation was quantitated by the fluorometric assay (FIG. 6A). Fluorescence values represent the amount of amyloid formed. FIGS. 6B and 6C provide electron micrographs of the nonincubated (FIG. 6B) and incubated fibrils for 24 hours with anti-amyloid peptide 1 (FIG. 6C). Magnification is 50,000×.

FIGS. 7A–C show the physio-chemical characterization of the amphoteriN (HMG-1) derived amyloid fragment, $ATN_p$. FIG. 7A provides the amino acid sequence of the fragment $ATN_p$ (SEQ ID NO: 11). Hydrophobic amino acid residues are highlighted in bold. FIG. 7B shows the Chou-Fasman prediction for β-sheet structure of $ATN_p$. The sequence with the highest β-sheet structure probability is indicated with a bar. FIG. 7C is an electron micrograph of negative-stained preparations of $ATN_p$ with formed amyloid-like fibrils.

FIG. 14A shows the effect of different molar ratios of iAβ or control peptide on fibril disassembly after 24 h of incubation. FIG. 14B fibril dissolution induced by a 40-fold molar excess of iAβ or control peptide after different incubation periods at room temperature.

FIG. 15a shows Aβ incubated for 6 days; FIG. 15b shows Aβ incubated with iAβ for 6 days; FIG. 15c shows Aβ incubated alone for 5 days and then for 1 day with iAβ; FIG. 15d shows iAβ incubated for 6 days at the same concentration as in FIGS. 15b and c; FIG. 15e shows Aβ incubated with the control peptide for 6 days; and FIG. 15f shows control peptide incubated alone for 6 days at the same concentration used in FIG. 15e.

DETAILED DESCRIPTION OF THE PREFERRED EMBODIMENTS

Novel peptides specifically designed to interfere with the β-sheet conformation of precursor proteins or peptides involved in the formation of amyloid or amyloid-like deposits were developed. The present invention is directed to these novel peptides, pharmaceutical compositions containing one or a mixture of such peptides of the invention, and methods for preventing, treating, or detecting disorders or diseases associated with abnormal protein folding into amyloid or amyloid-like deposits.

Figures 1A, 1B:
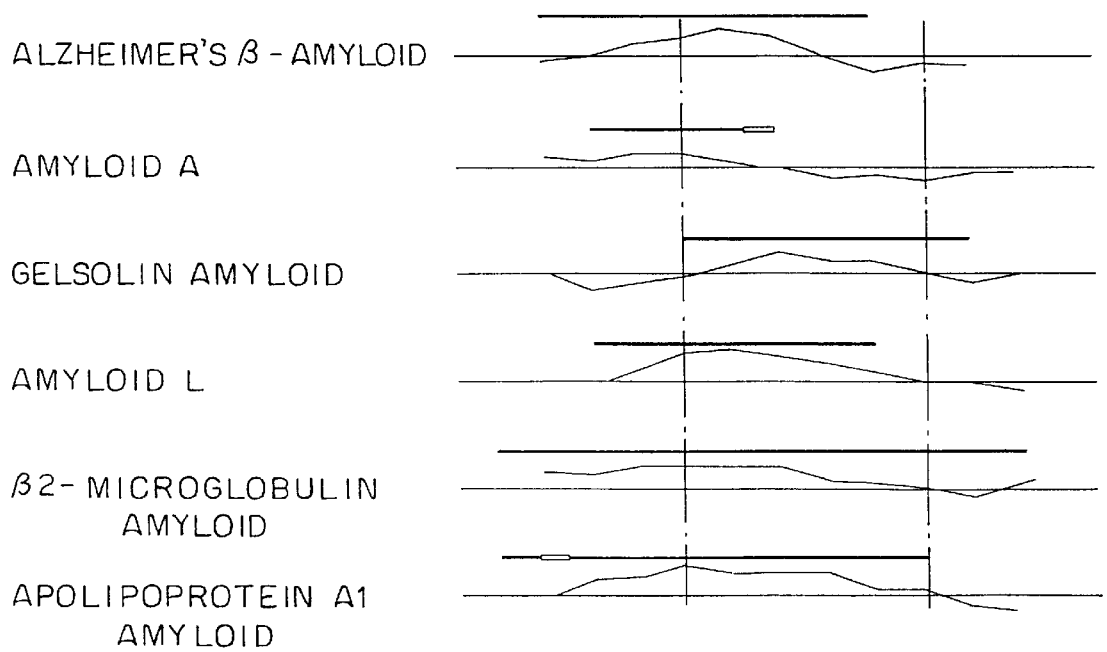
FIGS. 1A–B provide a consensus sequence for amyloidogenesis in terms of hydrophobicity and secondary structure properties.
Figure 3:
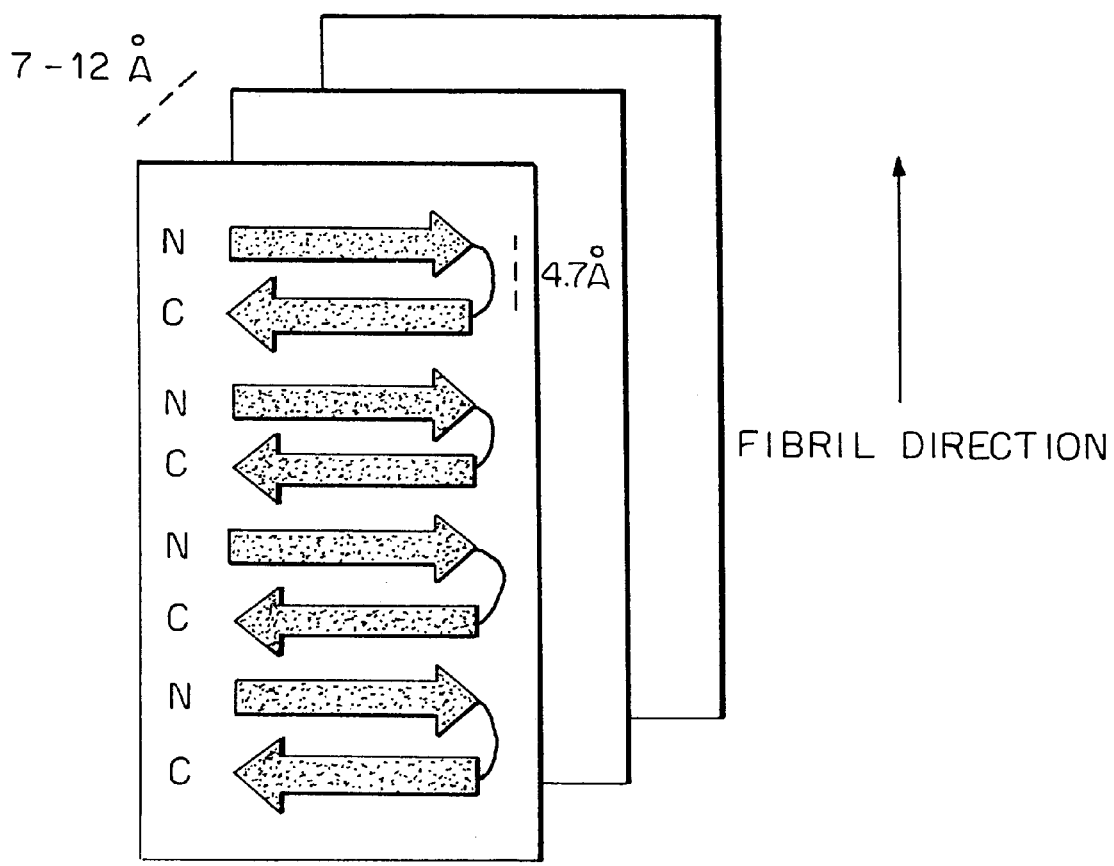
FIG. 3 is a schematic representation of the β-cross conformation for amyloid fibrils showing the crucial importance of the interactions by hydrogen bonding between the monomeric β-strand to form the intermolecular β-cross structure.
Figure 4A:
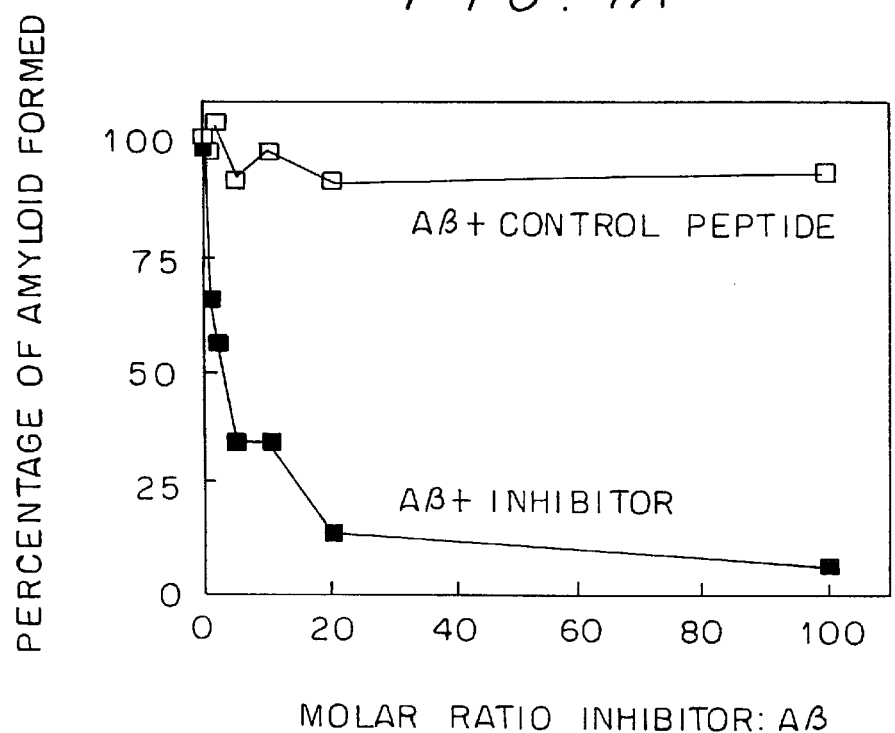
FIGS. 4A–4B show the effect of anti-amyloid peptide 1 having the sequence of SEQ ID NO: 7 on the amyloid formation by Aβ in vitro. Amyloid formation was quantitated by the fluorometric assay described in Example 1.
Figure 4B:
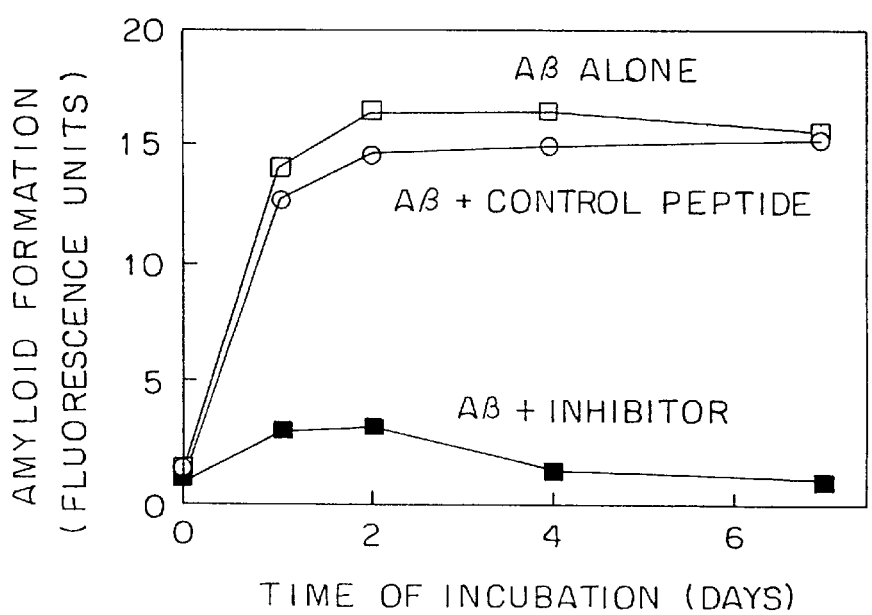
Figure 5A:
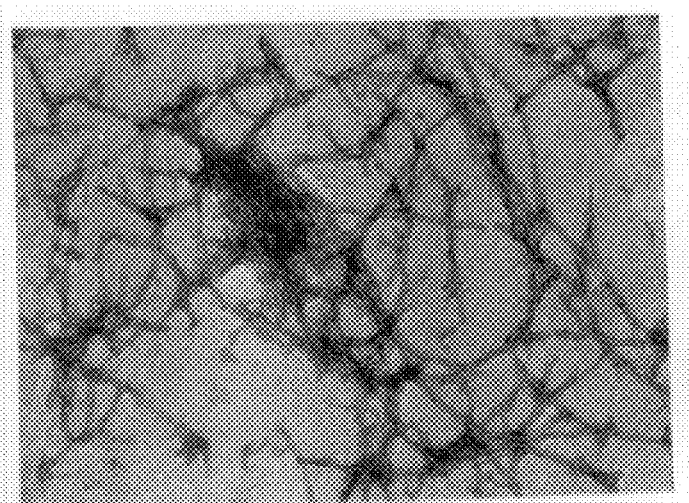
FIGS. 5A–C show electron micrographs of negative-stained preparations of Aβ (FIG. 5A), Aβ incubated with anti-amyloid peptide 1 (FIG. 5B) and anti-amyloid peptide 1 alone (FIG. 5C). Aliquots of Aβ were incubated at 1 mg/ml with or without the anti-amyloid peptide 1 in a molar ratio 1:50 (Aβ:anti-amyloid) for 6 days at room temperature.
Figure 5B:
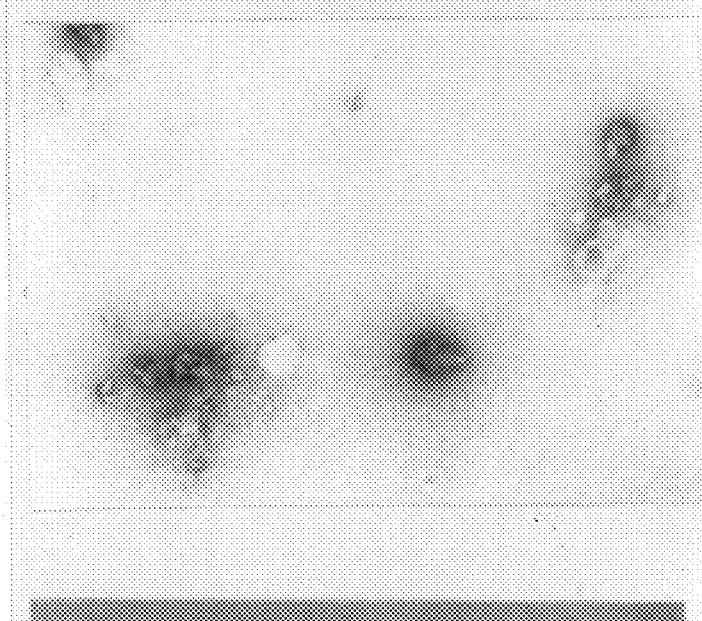
Figure 5C:
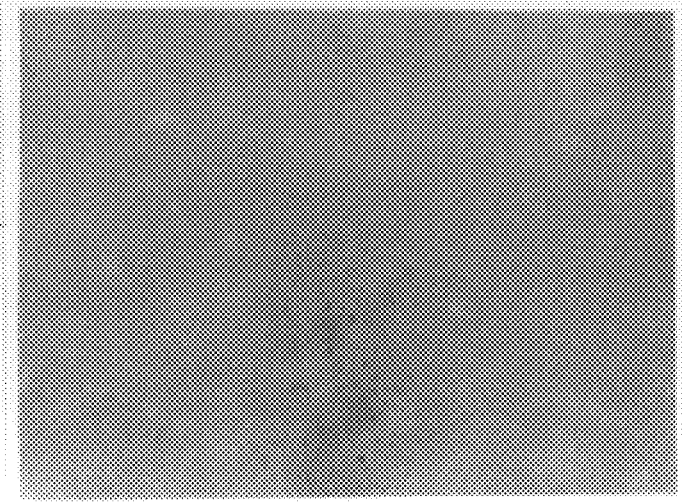
Figure 7C:
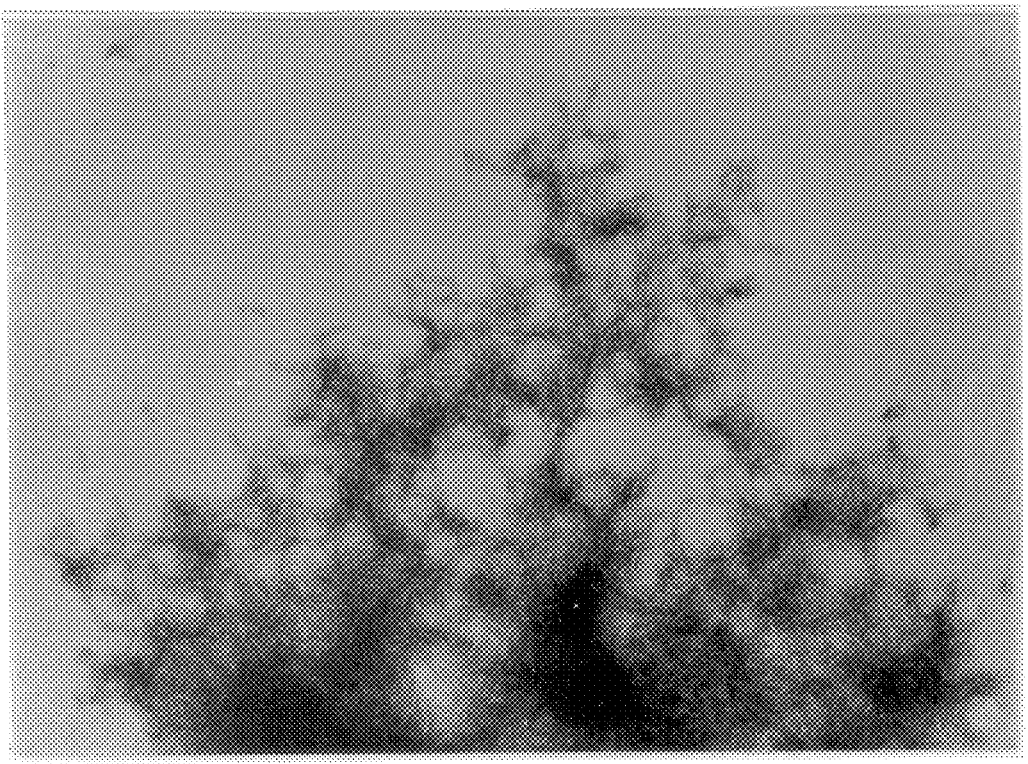

It has now been found that while the amino acid sequence of proteins from different amyloid or amyloid-like deposits differ, all of these amyloidogenic proteins or peptides contain a segment having the common characteristic of a hydrophobic cluster of hydrophobic amino acids (mainly phenylalanine, valine, alanine, leucine, isoleucine) being present within a larger segment strongly predicted to have a β-sheet conformation (FIGS. 1A and 1B). The hydrophobic cluster is believed to determine the binding of protein or peptide monomers resulting in aggregation, whereas the longer sequence, of which the hydrophobic cluster is a part, is believed to control the ordering of the aggregates into a β-cross conformation (β-cross quaternary fibril structure) typical of amyloid fibril structure (FIG. 3). Even a non-amyloid related peptide, which contains a potential amyloidgenic sequence motif (FIGS. 7A and 7B) such as obtained by proteolysis of amphoterin, forms typical amyloid-like fibrils in vitro (FIG. 7C).

The novel peptides of the present invention contain at least three hydrophobic amino acid residues forming a so-called "hydrophobic cluster". In addition, these novel peptides may contain more than three hydrophobic amino acid residues within the hydrophobic cluster, and/or may contain other amino acid residues outside of the hydrophobic cluster that also act to lower the propensity of the peptide to adopt a β-sheet conformation and/or increase the solubility of the peptide in an aqueous physiological medium. Preferably, the peptides of the present invention have a sequence of between three and fifteen amino acid residues and contain a hydrophobic core of three to eight hydrophobic amino acid residues in the middle of the sequence in addition to a charged amino acid residue, such as aspartic acid, glutamic acid, arginine, or lysine, at one end of the peptide. Most preferably, a charged hydrophilic amino acid residue is present at both ends of the peptide.

While prion protein PrP normally assumes an aα-helical conformation, it is believed that abnormal protein folding alters the normal PrP conformation to an abnormal β-sheet conformation. In any event, inhibitor peptides designed to bind to PrP prevents abnormal protein folding into a altered conformation resulting in amyloid or amyloid-like deposit.

In this invention, the peptides capable of interacting or binding with a structural determinant on a protein or peptide involved in amyloid or amyloid-like deposit formation, which inhibits the abnormal folding of the protein or peptide, were designed with a knowledge of the structural determinants for amyloid formation. Peptides having a hydrophobic region which interacts with a structural determinant of the protein or peptide, but with a very low probability of adopting a β-sheet conformation, are designed to bind to the structural determinant and function as an inhibitor of amyloid fibril formation or as an agent that dissolves preformed amyloid fibrils.

The peptides of the invention also contain at least one β-sheet blocking amino acid, such as Pro, Gly, Asn, or His, within the hydrophobic cluster so as to prevent the binding of protein or peptide monomers into aggregates and the ordering of such aggregates into an altered conformation such as the β-cross conformation typical of amyloid fibril structure. While the peptides can be designed to be partially homologous to the structural determinant they are to interact with, amino acid homology is unnecessary as long as the peptide have a hydrophobic core or cluster of sufficient hydrophobicity so that it will interact strongly with the structural determinant to structurally block abnormal protein or peptide folding into fibril deposits.

It will be appreciated by those in the art that besides the twenty common naturally occurring amino acids, modified amino acids or naturally occurring but rare amino acids can also be incorporated into the peptides of the present invention. For instance, it was demonstrated that a peptide with amino acid residues in the D-form inhibited fibrillogenesis of Aβ just as well as the peptide with the same sequence of amino acids in the L-form (see Example 1).

Modifications to amino acids in the peptides of the invention include, but are not limited to, an amide moiety or a pyroglutamyl residue. These modifications may contribute to decreasing the propensity to form β-sheet conformation or may contribute to peptide stability, solubility, or even immunogenicity. A more stable, soluble and less immunogenic peptide is desirable. Many neuropeptides modified at the C-terminus with a $CONH_2$ (amide) group appear to be resistant to attack by carboxypeptidases and many neuropeptides having a pyroglutamyl residue at the N-terminus are more resistant to attack by broad specificity aminopeptides. Also included as peptides of the present invention are cyclic peptides that are resistant to attack by both carboxypeptidases and aminopeptidases.

Non-limiting examples of peptides designed to inhibit abnormal folding in the formation of amyloid and amyloid-like deposits are presented in Table 1. The anti-PrP peptides are designed to bind to the structural determinant of PrP corresponding to amino acid residues 114 to 125 of prion (presented as SEQ ID NO:23). While Pro is used as the β-sheet blocking amino acid in the peptides presented in Table 1, it is expected that other β-sheet blockers, such as Gly, Asn and His, are suitable and would work equally well.

TABLE 1

Examples of Peptides Inhibiting Abnormal Protein Folding

1. Anti-amyloid peptides
    SEQ ID NO:7
    SEQ ID NO:8   (iAβ)
    SEQ ID NO:9
    SEQ ID NO:10
  a) shorter derivatives of iAβ (SEQ ID NO:8)
    SEQ ID NO:15
    SEQ ID NO:16
    SEQ ID NO:17
    SEQ ID NO:18
    SEQ ID NO:19
    Pro-Phe-Phe
  b) derivatives of iAβ with higher hydrophobicity
    SEQ ID NO:20
    SEQ ID NO:21
    SEQ ID NO:22
2. Anti-prion (PrP) peptides
    SEQ ID NO:24
    SEQ ID NO:25

It is preferable that a structural determinant is identified and a peptide is designed having a hydrophobic core or cluster which can bind to the structural determinant and structural block abnormal folding and prevent the formation of fibril deposits. However, the prior identification of the structural determinant may not always be necessary.

Methods for predicting protein conformation to aid in the design of peptide that have a hydrophobic cluster and a low probability of abnormally folding into an altered conformation such as a β-sheet are described in Chou and Fasman *Ann. Rev. Biochem.* 47:251–276, 1978, Garnier et al., *J. Mol. Biol.* 120:97–120, 1978, and Minor et al. *Nature* 371:264–267, 1994.

As a method of preventing or treating a disorder or disease associated with amyloid or amyloid-like deposits, the inhibitory peptide of the present invention is administered in an effective amount to a subject in need thereof, where the subject can be human or animal. Likewise, a method of detecting such disorders or diseases also includes administering a sufficient amount of the designed peptide to visualize its binding to fibril deposits by well known imaging techniques.

As used herein, the term "prevention" of a condition, such as Alzheimer's disease or other amyloidosis disorders, in a subject involves administering a peptide according to the present invention prior to the clinical onset of the disease. "Treatment" involves administration of the protective peptide after the clinical onset of the disease. For example, successful administration of the peptide of the present invention, after development of a disorder or disease comprises "treatment" of the disease. The invention is useful in the treatment of humans as well as for veterinary uses in animals.

The peptides of the present invention may be administered by any means that achieves its intended purpose. For example, administration may be by a number of different parenteral routes including, but not limited to, subcutaneous, intravenous, intradermal, intramuscular, intraperitoneal, intracerebral, intranasal, oral, transdermal, or buccal routes. Parenteral administration can be bolus injection or by gradual perfusion over time.

A typical regimen for preventing, suppressing, or treating a condition associated with amyloid or amyloid-like deposits, comprises either (1) administration of an effective amount in one or two doses of a high concentration of inhibitory peptides in the range of 0.5 to 10 mg of peptide, more preferably 0.5 to 5 mg of peptide, or (2) administration of an effective amount of the peptide administered in multiple doses of lower concentrations of inhibitor peptides in the range of 10–1000 µg, more preferably 50–500 µg over a period of time up to and including several months to several years.

It is understood that the dosage administered will be dependent upon the age, sex, health, and weight of the recipient, kind of concurrent treatment, if any, frequency of treatment, and the nature of the effect desired. The total dose required for each treatment may be administered by multiple doses or in a single dose. By "effective amount", it is meant a concentration of inhibitor peptide(s) which is capable of slowing down or inhibiting the formation of amyloid or amyloid-like deposits, or of dissolving preformed fibril deposits. Such concentrations can be routinely determined by those of skill in the art. It will also be appreciated by those of skill in the art that the dosage may be dependent on the stability of the administered peptide. A less stable peptide may require administration in multiple doses.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

Pharmaceutical compositions comprising the peptides of the invention include all compositions wherein the peptide (s) are contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically. Suitable pharmaceutically acceptable vehicles are well known in the art and are described for example in Gennaro, Alfonso, Ed., *Remington's Pharmaceutical Sciences*, 18th Edition 1990, Mack Publishing Co., Easton, Pa., a standard reference text in this field. Pharmaceutically acceptable vehicles can be routinely selected in accordance with the mode of administration and the solubility and stability of the peptides. For example, formulations for intravenous administration may include sterile aqueous solutions which may also contain buffers, diluents and other suitable additives.

Suitable formulations for parenteral administration include aqueous solutions of the active compounds in water-soluble form, for example, water-soluble salts. In addition, suspension of the active compound as appropriate oily injections suspensions may be administered. Suitable lipophilic solvents or vehicles include fatty oils, for example, sesame oil, or synthetic fatty acid ester,s for example ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

Disorders or diseases associated with abnormal protein folding into amyloid or amyloid-like deposits to be treated or prevented by administering the pharmaceutical composition of the invention includes, but is not limited to, Alzheimer's disease, FAF, Down's syndrome, other amyloidosis disorders, human prion diseases, such as Kuru, Creutzfeldt-Jakob Disease (CJD), Gerstmann-Straussler-Scheinker Syndrome (GSS), prion associated human neurodegenerative diseases as well as animal prion diseases such as scrapie, spongiform encephalopathy, transmissible mink encephalopathy and chronic wasting disease of mule deer and elk.

Besides preventative and therapeutic treatments, the peptides of the invention may also be administered to detect and diagnose the presence or absence of amyloid or amyloid-like deposits in vivo. A designed peptide capable of binding to structural determinants in a corresponding amyloid or amyloid-like deposit, labeled non-radioactively or with a radioisotope, as is well-known in the art, can be administered to a subject for diagnosing the onset or presence of a disease or disorder associated with abnormal protein folding into amyloid or amyloid-like fibril deposits. The binding of such a labeled peptide after administration to amyloid or amyloid-like deposits can be detected by in vivo imaging techniques known in the art.

Having now generally described the invention, the same will be more readily understood through reference to the following example which is provided by way of illustration and is not intended to be limiting of the present invention.

EXAMPLE 1

Amyloid deposition appears to be an important factor in the development of neuritic plaque and neuronal disfunction in AD. The results of the study presented below indicate that a short peptide partially homologous to the central hydrophobic region of Aβ (residues 17–21), but containing amino acids which block the adoption of a β-sheet structure binds Aβ, inhibits amyloid formation in vitro and dissolves preformed Aβ fibrils. Furthermore, the inhibitor is able to block the in vivo deposition of AA in the spleen of mice. Since the inhibition of fibrillogenesis and the disassembly of preformed fibrils occurs in the presence of a molar excess of an 11 amino acid peptide, called inhibitor of Aβ fibrillogenesis peptide (iAβ) and also designated as anti-amyloid peptide 2, the Aβ-Aβ interaction probably has a greater affinity that the Aβ-iAβ interaction. Although a molar excess of iAβ is required to produce the inhibition of amyloid formation the very low concentration of sAβ present in human body fluids (1–10 nM) would necessitate only 40–400 nM of iAβ for a 4-fold molar excess.

The results of the study support the concept that the formation of a β-sheet secondary structure is important for fibrillogenesis and we believe that iAβ inhibits amyloid formation by binding to monomeric Aβ peptides thereby blocking the formation of the oligomeric β-sheet conformation precursor of the fibrils. The dissolution of preformed fibrils induced by iAβ may indicate that the monomeric peptide is in equilibrium with the fibrils, as previously suggested (Levin, M. et al., *J. Clin. Invest.* 51:2773–2776, 1972; Kisilevsky, R. et al., *Lab. Invest.* 48:53–59, 1983). The inhibitor may bind to monomeric peptide, thus displacing the equilibrium, and leading to fibril disaggregation.

Material and Methods

Peptide synthesis

Synthetic peptides containing the sequence 1-40, 1-42 of Aβ and the anti-amyloid peptides were synthesized by a solid phase technique on a p-methyl-benzhydrylamine resin using a Biosearch SAM 2 synthesizer. Peptides were subjected to purification by high performance liquid chromatography (HPLC) with the use of a reverse-phase support medium (Delta-Bondapak) on a 0.78×30 cm column with a 0–80% linear gradient of acetonitrile in 0.1% (v/v) trifluoroacetic acid. The peptide content of the eluate was monitored by measurement of its absorption at 220 nm. Peptide sequences were determined by automatic Edman degradation on a 477A protein sequencer and the PTH derivatives analyzed with an on-line 120 A PTH analyzer (Applied Biosystems, Foster City, Calif.). Purity of the peptides was evaluated by peptide sequencing and laser desorption mass spectrometry. Stock solutions of the peptides were prepared by dissolving them in 50% acetonitrile. The concentration was determined by amino acid composition analysis on a Waters Pico-Tag amino acid analyzer (Millipore Corp, Bedford, Mass.), after hydrolyzing the samples under reduced pressure in the presence of 6M HCl for 20 hours at 110° C. For experiments, peptide aliquots were lyophilized and resuspended in the buffer used in the assay.

Prediction of Secondary Structure

The α-helix, β-sheet and β-turn propensities for different sequences were calculated by the Chou and Fasman secondary structure prediction algorithm (Chou and Fasman, *Ann. Rev. Biochem.* 47:251–2760, 1978) using the program Protylze version 3.01 from Copyright.

Fluorimetric determination of amyloid formation

Aliquots of peptides were incubated for varying amounts of time at room temperature in 0.1M Tris-HCl, pH 7.4. To quantitate amyloid formation, a thioflavine T (ThT) fluorescence method was used. ThT binds specifically to amyloid and this binding procedure produces a shift in its emission spectrum and a fluorescent signal proportional to the amount of amyloid formed (Naiki et al., *Lab. Invest.* 65:104–110, 1991). Thus, this method is very specific for the semiquantitation of amyloid-like aggregates. After incubation Aβ peptides were added to 50 mM glycine, pH 9.2, 2 μM ThT in a final volume of 2 ml. Fluorescence was measured at an excitation wavelength of 435 nm and an emission wavelength of 485 nm using a Hitachi F-2000 fluorescence spectrometer (Hitachi Instruments Inc., San Jose, Calif.). A time scan of fluorescence was performed and three values after the decay reached the plateau (280, 290 and 300 seconds) were averaged after subtracting the background fluorescence of 2 μM ThT.

Electron microscopy

For fibril formation, peptides (1 mg/ml) were incubated in 0.1 M Tris-HCl, pH 7.4, for 6 days at room temperature. Samples to be visualized were placed on carbon formvar-coated 300-mesh nickel grids for 1 minute, blotted and stained for 1 minute with 2% uranyl acetate under a vapor of 2% glutaraldehyde and visualized on a Zeiss EM 10 electron microscope (Carl Zeiss, Inc., Thornwood, N.Y.) at 80 kV.

Circular dichroism studies

The secondary structure of Aβ and inhibitor peptides was analyzed by circular dichroism in aqueous solution. Spectra were recorded in a Jasco spectropolarimeter Model J-720 (Jasco Inc., Easton, Md.). Aliquots of peptides at a concentration of 0.1–0.2 mg/ml in 20 mM Tris-HCl, pH 7.4, were first centrifuged to produce a clear solution and the spectra were recorded at 1 nm intervals over the wavelength range 190 to 260 nm in a 0.1 cm pathlength cell. Results are expressed in terms of mean residue ellipticity in units of deg $cm^2 dmol^{-1}$.

Binding sites

The interaction between Aβ an iAβP was studied by fluorescence spectroscopy at 25° C. using a Perkin Elmer model LS50B spectrofluorimeter. 45 μg of Aβ1-40 was dissolved in 300 μl of 5 mM Tris, pH 7.4 and immediately the fluorescence spectra was recorded between 290 nm an 400 nm at excitation 280 nm, with slits set at 2.5 nm bandwidth. Different amounts of lyophilized iAβ were added to the Aβ solution and after 15 min of incubation the fluorescence spectra was recorded, iAβ at the same concentrations did not give any fluorescence signal above the background. The binding of iAβ to Aβ was evaluated by the change in fluorescence intensity at 309 nm between the spectra of Aβ alone and in the presence of different concentrations of the inhibitor. The binding data were analyzed with the aid of a curve fitting software (GraphPad Prism version 1.0).

Fluorometric quantitation of fibrillogenesis

The assay used was based on fluorescence emission by ThT, as described previously (Burdick et al., 1992, supra). Aliquots of Aβ at a concentration of 1 mg/ml prepared in 0.1M Tris, pH 7.4 were incubated for different times in the absence or in the presence of different concentrations of iAβ. In order to evaluate the inhibition of amyloid formation and dissolution of preformed fibrils, the inhibitor peptide was added at the beginning of the incubation or after 6 days of incubation of Aβ alone. At the end of the incubation period, 50 mM glycine, pH 9.2, 2 μM thioflavine T was added in a final volume of 2 ml. Fluorescence was measured at excitation 435 nm and emission 485 nm in a Perkin Elmer, model LS50B fluorescence spectrometer.

In vivo studies using the experimental murine model of amyloidosis

Induction of experimental amyloidosis was done as previously described (LeVine et al., *Protein Sci.* 2:404–410, 1993; Snow et al., *J. Histochem. Cytochem.* 39:1321–1330, 1991). BALB/c mice were injected t.v. with 100 μg of amyloid enhancing factor (AEF) alone or preincubated for 24 h with 5 mg of iAβ. AEF was prepared using the standard protocols (Merlini et al., *Proc. Natl. Acad. Sci. USA* 92:2959–2964, 1995). The AEF injection was followed by a single s.c. injection of 0.5 ml of 2% silver nitrate. Animals were sacrificed 5 days after the injection and the amyloid quantitated by immunohistochemistry and congo red staining. A standard set of amyloid containing tissue was generated (5%, 10%, 20%, 30%, 40%, 50). These were reference points to determine the amount of amyloid in a given tissue. Standard sections were examined under the microscope (Nikon, using polarizing filters to generate birefringence for Congo red). The images were digitized and transferred to a MacIntosh computer for analysis. The digitized images were analyzed for color (intensity and area) under low power (20×) using a Kontron or Prism Image Analysis. Experimental spleen tissue sections were fixed in 10% buffered formalin and embedded in paraffin and stained with antibodies against SAA. The experimental sections were analyzed and compared to the standards for quantitation of the area spleen containing amyloid. The experiments were performed using four animals per condition.

Results

Design of inhibitor peptides

Figures 2A, 2B:
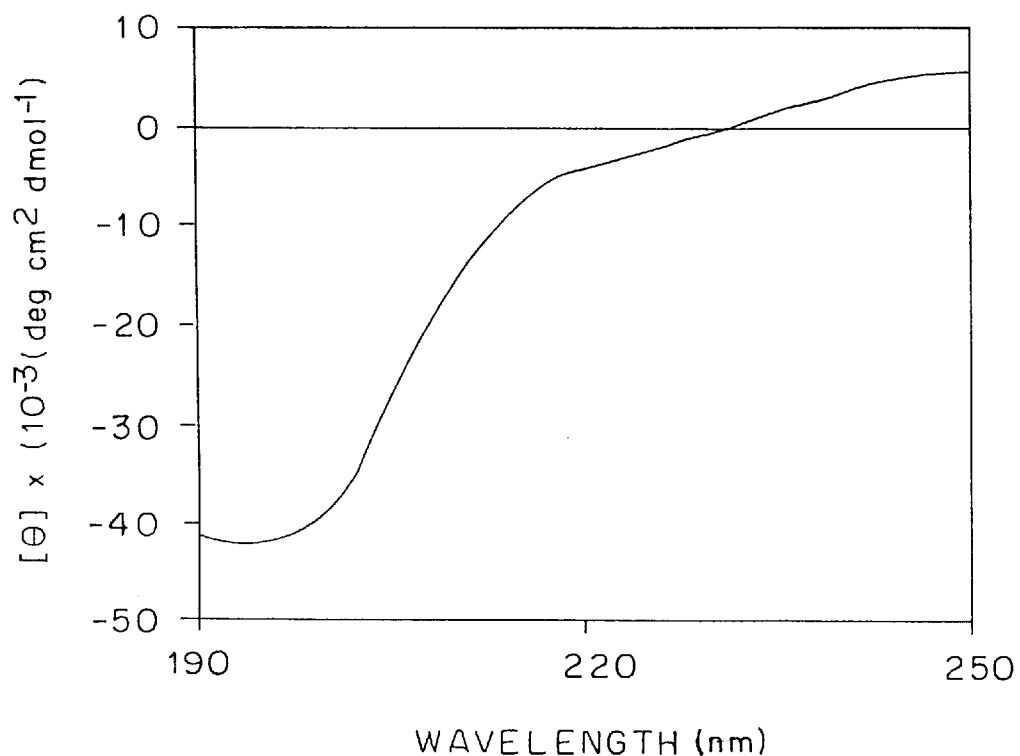
FIGS. 2A–B provide the amino acid sequence for several anti-amyloid peptides.
Figure 9:
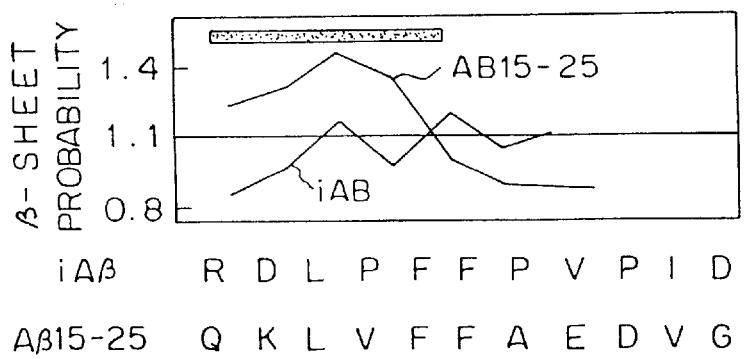
FIG. 9 shows the structural characteristics of iAβ. The amino acid sequence and β-sheet probability for iAβ (SEQ ID No: 8) and for the region of Aβ (SEQ ID No: 14) used as a template for iAβ is shown underneath the β-sheet probability profile where the solid bar represents the region of Aβ having a high probability of β-sheet structure.

Our laboratory focused on the central hydrophobic region within the N-terminal domain of Aβ, amino acids 17–21 (corresponding to amino acid residues 2–6 of SEQ ID NO:1), as a model for our inhibitor peptide (FIGS. 2A and 9). Proline residues were introduced in the inhibitor peptide in order to block β-sheet structure and charged residues were added at the ends of the peptide to increase solubility. Proline was chosen to block β-sheet structure since it rarely forms part of this conformation (Chou et al., *Ann. Rev. Biochem.* 47:251–276, 1978) and does not occurs in the interior of antiparallel β-sheets (Wouters et al., *Protein Sci.* 3:43S, 1994), due to the extraordinary characteristics of this amino acid, namely: (a) the nitrogen of the peptide bond is not available to the β-sheet bonding network; (b) the torsion angles of the peptidyl-propyl bond imposed by the proline ring are incompatible with peptide bond geometries found in β-sheet motifs; and (c) the proline ring can not fit sterically within the β-sheet bonding network. Moreover, recent data showed that the introduction of proline residues into short peptides homologous to Aβ resulted in non-amyloidogenic analogues ((Wood et al., *Biochem.* 34:724–730, 1995).

Figure 10:
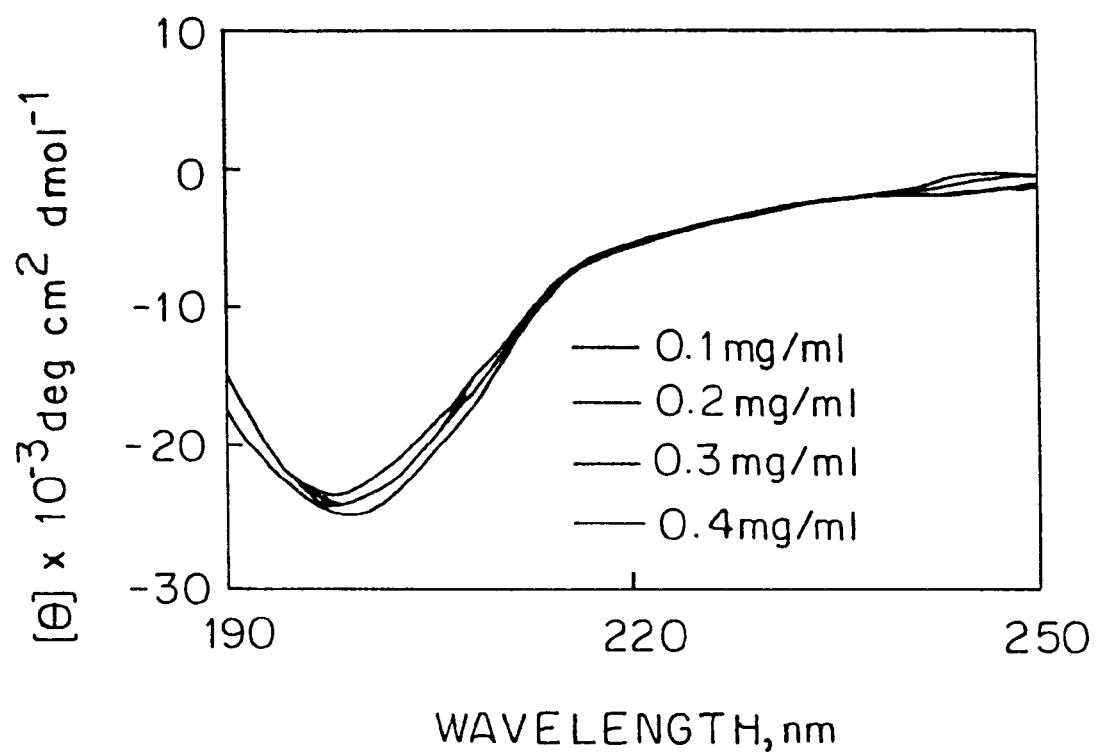
FIG. 10 shows the circular dichroism spectra of iAβ at different peptide concentration.

Based on these criteria, an 11 amino acid peptide, called inhibitor of Aβ fibrillogenesis peptide (iAβ) was designed, which has a low probability of adopting a β-sheet conformation due to the presence of proline residues (FIG. 9). Other peptide inhibitors based on the above criteria are shown in FIG. 2A. The circular dichroism spectrum of iAβ in aqueous solution was typical of unordered structures (FIG. 10). Samples of iAβ at different concentrations as well as samples incubated for several days have similar spectra (FIG. 10). Indeed, iAβ did not aggregate even at high concentrations (4 mg/ml) or after long periods of incubation (more than 30 days).

Figure 11A:
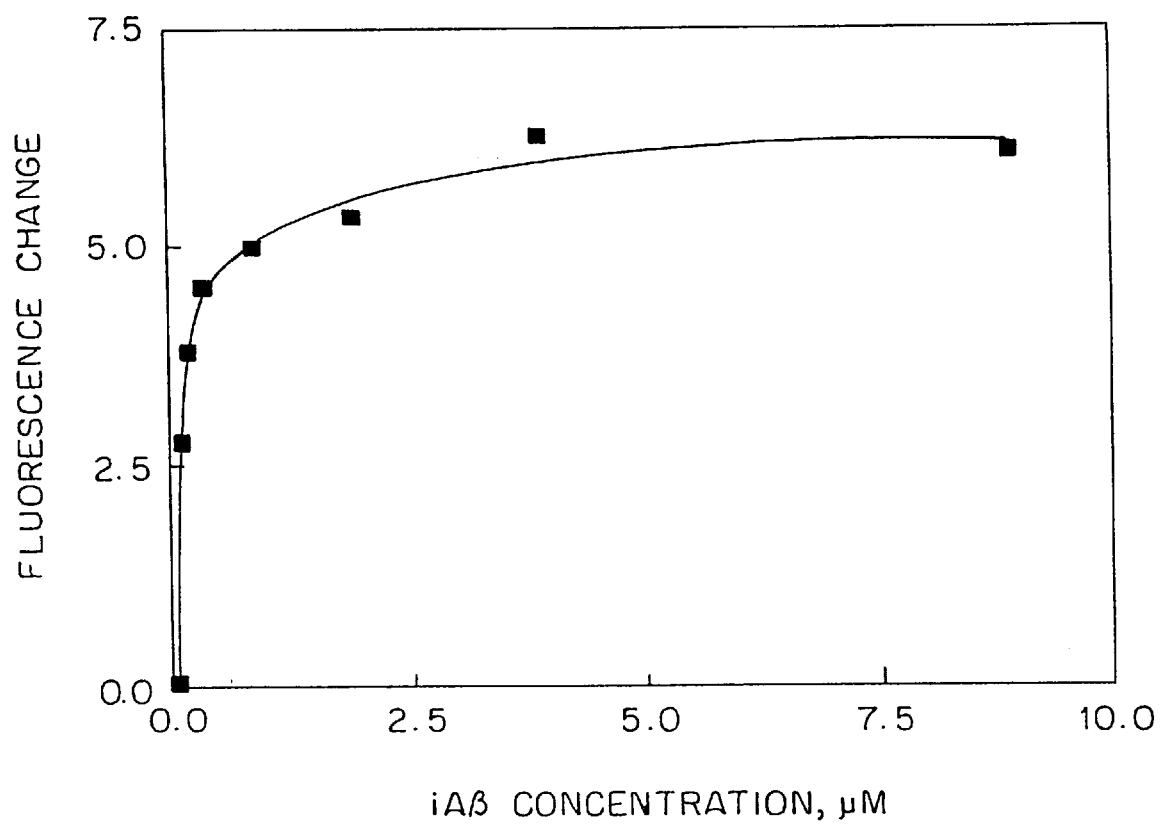
FIGS. 11A and 11B show the Aβ-iAβ interaction as quantitated by the quenching of the intrinsic fluorescence of Aβ (tyrosine 10) induced by the binding of iAβ (FIG. 11A) and the fluorescence spectra of Aβ incubated alone or in the presence of 4 μM iAβ (FIG. 11B).
Figure 11B:
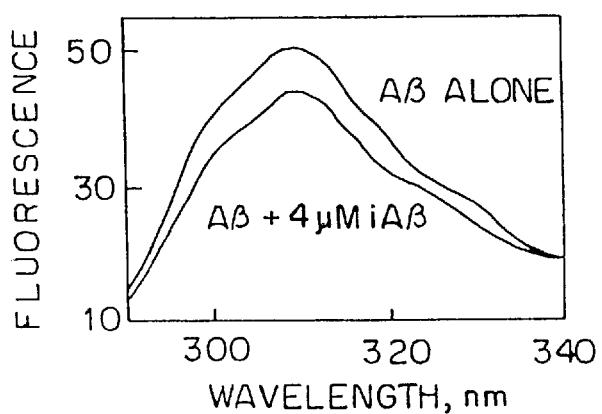

The interaction between Aβ and iAβ was studied by monitoring the quenching of $Tyr^{10}$ fluorescence of Aβ (FIG. 11A). Fluorescence spectroscopy was chosen to study the interaction of Aβ-iAβ because this technique has been used extensively for ligand-binding studies and does not require peptide labelling with reagents that may alter their properties. Aβ excited at 280 nm showed a fluorescence spectrum with a maximum at 309 nm (FIG. 11B, inset), which is typical of tyrosine emission. The presence of iAβ induced a saturable quenching of the fluorescence, reaching a maximum of 12.6% of the total fluorescence at approximately 4 $\mu$M of iAβ (FIG. 11A). Non-linear regression analysis of the binding data to a rectangular hyperbola allowed calculation of a relative dissociation constant of 75.9±6.5 nM.

Figure 12:
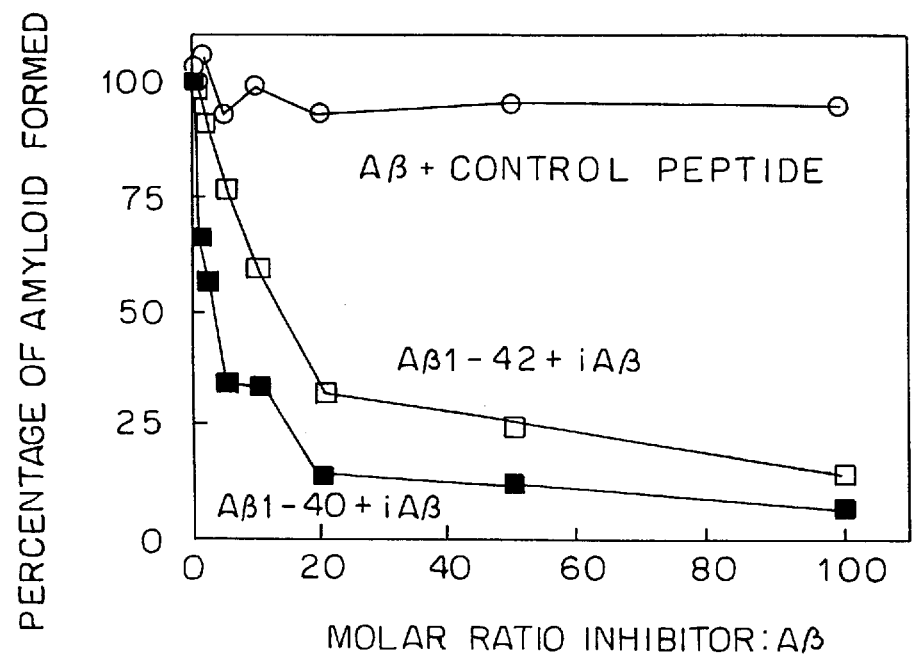
FIG. 12 shows the dose-dependent inhibition of Aβ1-40 and Aβ1-42 fibrillogenesis by iAβ. Amyloid formation was quantitated by the fluorometric assay, as described in Example 1. The Aβ concentration was 1 mg/ml in 0.1M Tris, pH 7.6 and an incubation time of 24 h.
Figure 13:
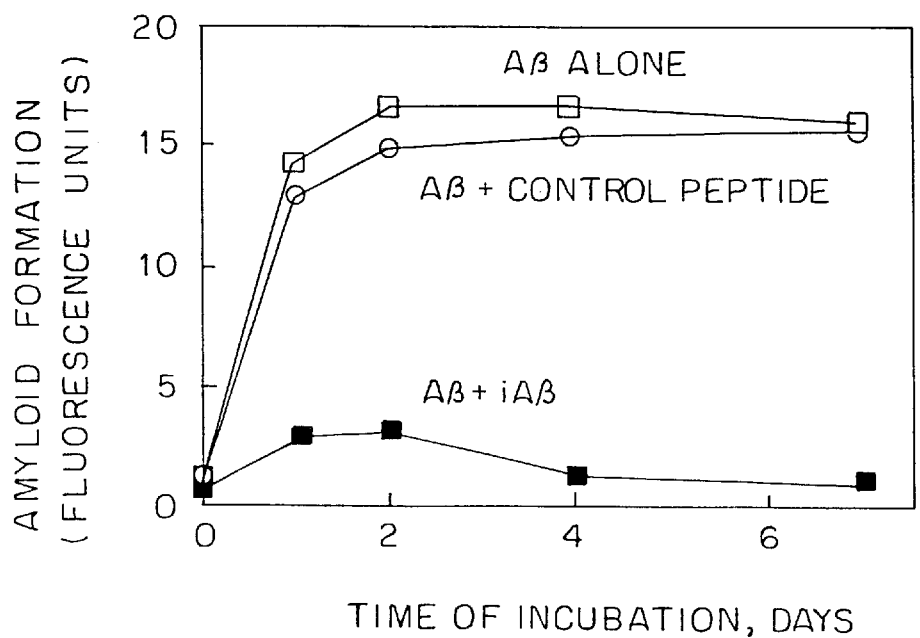
FIG. 13 shows the effect of iAβ on amyloid formation by Aβ1-40, after different incubation periods. The molar ratio Aβ:iAβ (or control) was 1:20; Aβ concentration 1 mg/ml. Amyloid formation was quantitated as in FIG. 12. iAβ or the control peptide alone did not give fluorescence values above the background level.

Inhibition of Aβ amyloid formation and dissolution of preformed fibrils in vitro The quantitative evaluation of the effect of iAβ on in vitro Aβ fibrillogenesis was based on a fluorometric assay that measures thioflavine T (ThT) fluorescence emission (Soto et al., 1995, supra). The binding of ThT to amyloid is specific and produces a shift in the emission spectrum of ThT and a fluorescent enhancement proportional to the amount of amyloid (LeVine et al., 1993, supra). FIG. 12 shows the influence of different concentrations of iAβ on fibrillogenesis of the two major variants of Aβ (Aβ1-40 and Aβ1-42). iAβ inhibited in a dose-dependent manner in vitro amyloid formation by both Aβ variants. After 24 h of incubation in the presence of a 5-fold or 20-fold molar excess of iAβ, Aβ1-40 formed only 33.9% and 13.7%, respectively, of the amyloid detectable in the absence of inhibitor (FIG. 12). Although the inhibitor is less efficient with Aβ1-42, a 5-, 20-, and 40-fold molar excess of iAβ over Aβ1-42 resulted in a 28.7%, 72.3% and 80.6% of inhibition, respectively (FIG. 12). Several non-related peptides had no effect on fibrillogenesis or slightly increased Aβ amyloid formation, probably by incorporation into the fibrils. The 12 residue control peptide (SEQ ID NO:26), did not alter amyloid formation by Aβ1-40 or Aβ1-42 (FIGS. 12 and 13). iAβ inhibited Aβ amyloid formation even after extensive incubation (FIG. 13) and appeared to be a more efficient blocker of fibrillogenesis after several days of incubation.

The 15-amino acid peptide, designated anti-amyloid peptide 1 (SEQ ID NO:7) was found to adopt a random coil conformation (FIG. 2B) and was also found to be 90% inhibitory to amyloid fibril formation at 50-fold molar excess over soluble amyloid monomers (FIGS. 4A, 4B, 5A and 5B).

Figure 14A:
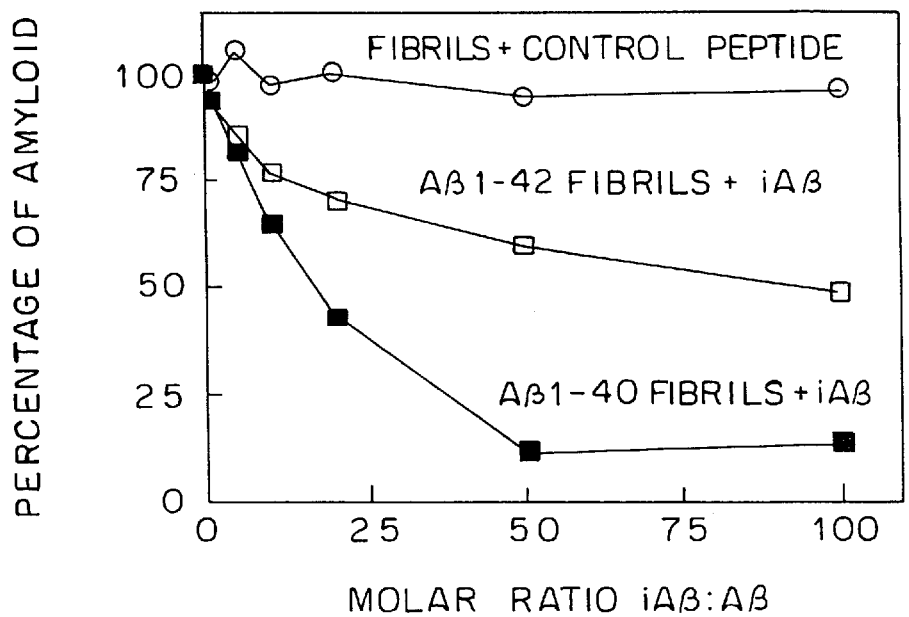
FIGS. 14A and 14B shows the dissolution of preformed Aβ fibrils by iAβ in vitro. Amyloid fibrils were first preformed by incubating Aβ1-40 or Aβ1-42 at a concentration of 1 mg/ml for 6 days at room temperature. Fluorometric quantitation of amyloid as described in Example 1.
Figure 14B:
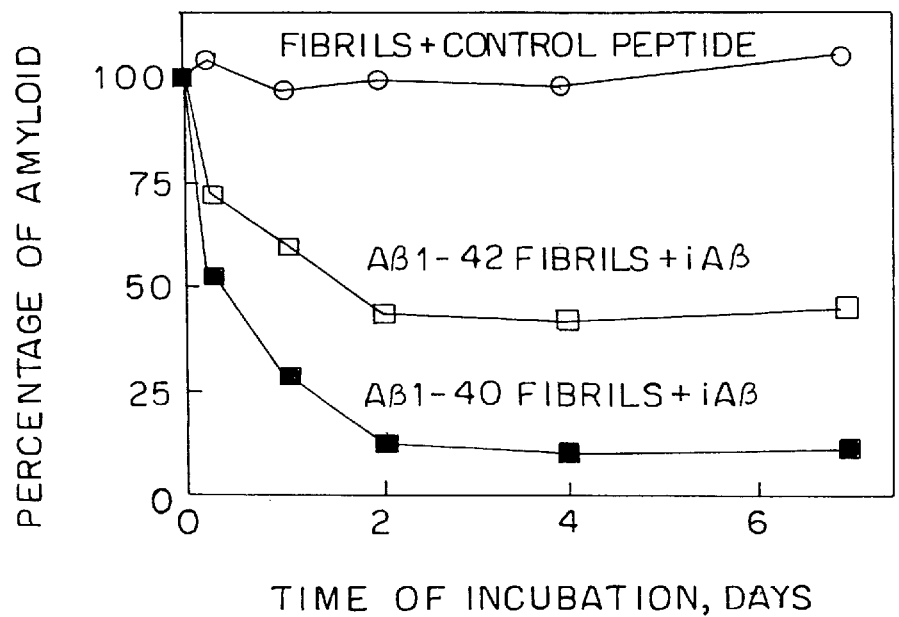

In order to evaluate the ability of iAβ to disassemble preformed Aβ fibrils, Aβ1-40 or Aβ1-42 (1 mg/ml) were preincubated for 5 days at 37° C. before the addition of inhibitor peptide. FIG. 14A shows the dissolution of Aβ1-40 or Aβ1-42 fibrils after 24 h incubation with different iAβ concentrations. The inhibitor efficiently affected disaggregation of Aβ1-40 fibrils, achieving almost complete dissolution when used in a 40-fold molar excess. Conversely, only 51% of Aβ1-42 fibril reduction was obtained with the same molar excess of iAβ (FIG. 14). The maximum level of fibril dissolution was obtained after 2 days of incubation with iAβ and remained unaltered thereafter (FIG. 14B).

Figure 17:
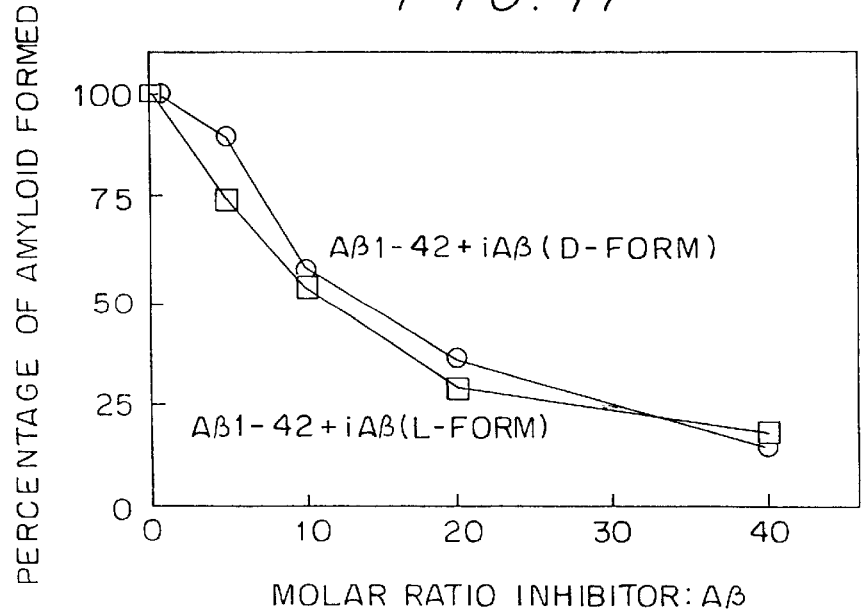
FIG. 17 shows the inhibition of Aβ fibrillogenesis by iAβ containing all D-amino acids.

The D-form of iAβ to inhibit Aβ fibrillogenesis was compared to the L-form of iAβ and the results shown in FIG. 17 demonstrate that D-iAβ inhibits Aβ fibrillogenesis similarly to L-iAβ. Aβ1-42 (1 mg/ml) was incubated for 24 h in the presence of different molar ratios of the L- and D-form of iAβ. Amyloid was quantitated by the fluorometric assay based on the thioflavine T fluorescence emission and expressed as a percentage of the amyloid obtained in the Aβ sample non-incubated with the inhibitor.

Figures 15A, 15B:
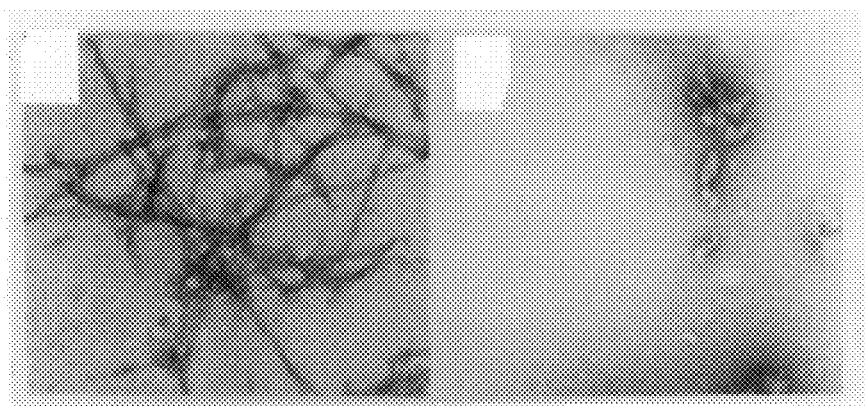
FIGS. 15a–f shows the electron microscopy analysis of the effect of iAβ on fibril formation and dissolution. Aliquots of Aβ1-40 (2 mg/ml) were incubated at 37° C. with or without iAβ or control peptide at a molar ratio 1:40 (Aβ:iAβ), centrifuged and the pellet loaded on electron microscopy grids, stained and visualized as described in the Materials and Methods.
Figures 15C, 15D:
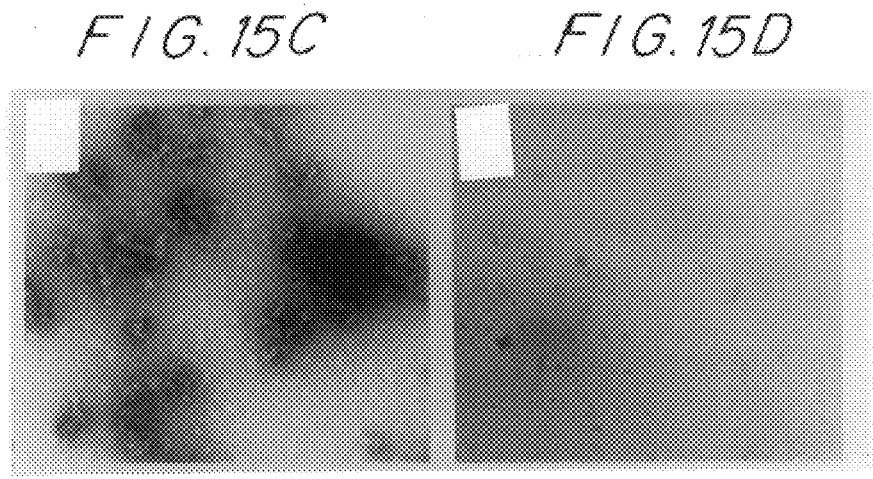
Figures 15E, 15F:
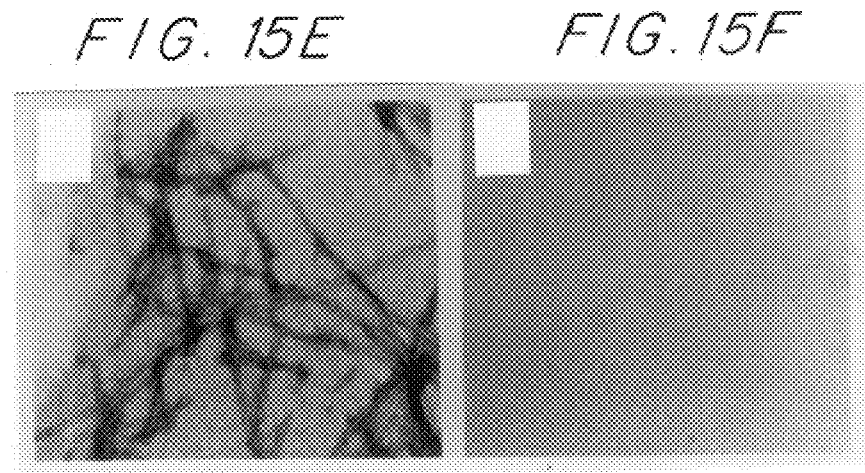
Figure 16:
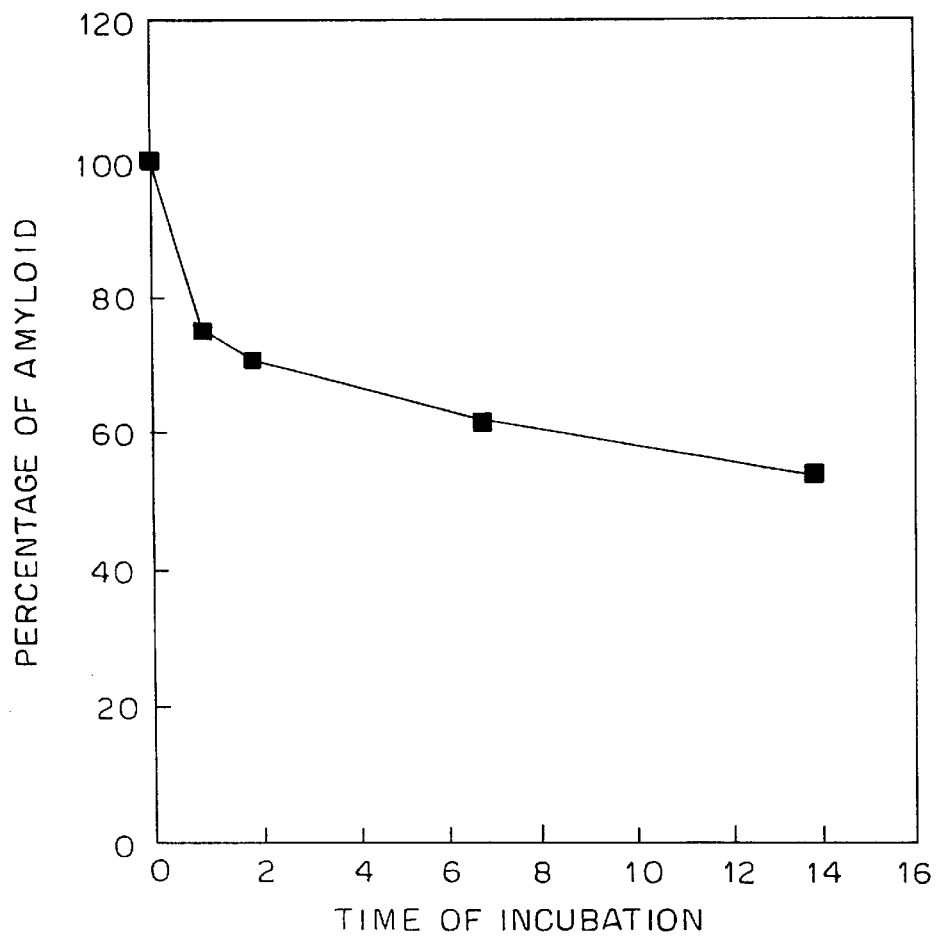
FIG. 16 shows the inhibition of amyloid formation after long period of incubation (days) in the presence of low concentrations of iAβ. 30 μg of Aβ1-42 was incubated in 30 μl of 0.1M tris, pH 7.4 with a molar ratio 1:5 (Aβ:iAβ) of the inhibitor for different times at room temperature. Amyloid was quantitated by the thioflavine T fluorometric assay and expressed as a percentage of the amount of amyloid incubated for the same time in the absence of the inhitor.

The inhibition of fibril formation and the dissolution of preformed fibrils by iAβ was also analyzed by negative-staining electron microscopy (FIGS. 15a–f). Aβ1-40 (2 mg/ml) preincubated for 6 days at 37° C. formed typical 8–10 nm unbranched fibrils (Castano et al., *biochem. Biophys. Res. Commun.* 141:782–789, 1986) (FIG. 15a). When Aβ was incubated from the start with a 40-fold excess of iAβ, only amorphous aggregates were obtained (FIG. 15b). The control peptide under the same conditions did not produce any effect on Aβ fibrillogenesis (FIG. 15e). Fibrils preformed by incubation of Aβ1-40 for 6 days at 37° C. were almost completely dissolved after 2 days of incubation with a 1:40 molar ratio of Aβ:iAβ (FIG. 15c). iAβ or the control peptide incubated under the same conditions used in the experiments shown in FIGS. 15b and 15e, formed no amyloid-like material (FIGS. 15d and 15f).

Figure 6B:
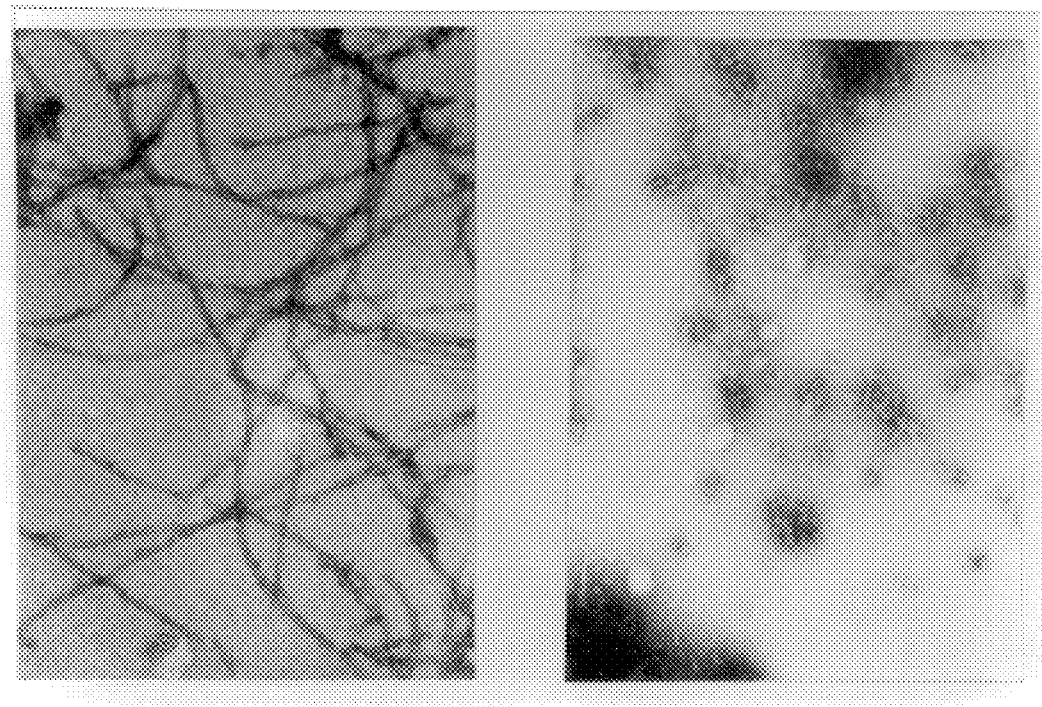
Figure 8:
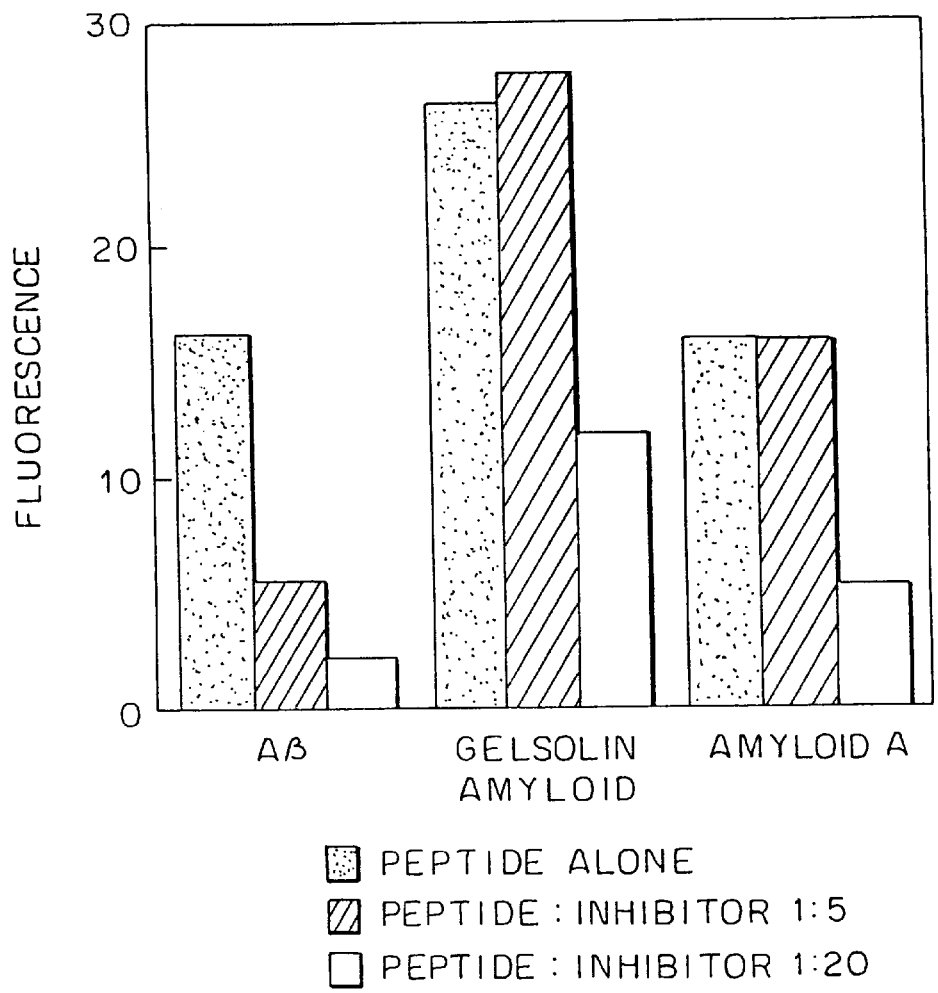
FIG. 8 is a bar graph showing the effect of anti-amyloid peptide 1 on the amyloid formation by Aβ and of peptides derived from the amyloidogenic sequence of gelsolin amyloid and amyloid A. Either Aβ or the fifteen amino acid peptides containing the amyloidogenic sequence of gelsolin amyloid (SEQ ID NO: 12) and amyloid A (SEQ ID NO: 13) were incubated in a concentration of 1 mg/ml for 24 hours without and with anti-amyloid peptide 1 in a molar ratio of 1:5 or 1:20.

Dissolution of preformed fibrils also occurred with the 15 amino acid anti-amyloid peptide 1 (FIGS. 6A–6C). This anti-amyloid peptide also inhibits the fibril formation of other amyloidogenic peptides derived from various other amyloid material, e.g., amyloid-A and the gelsolin related amyloid (FIG. 8).

Inhibition of in vivo fibrillogenesis using an animal model of amyloidosis related to amyloid-A A well-characterized mouse model for systemic amyloid-A (AA) deposition was used. This model has been used to test the role of amyloid-associated components such as proteoglycans and apolipoprotein E (Kindy et al., *Lab. Invest.* 73:469–476, 1995; Snow et al., 1991, supra) and to test inhibitors of amyloid deposition in vivo (Kisilevsky et al., *Nature Med.* 1:143–148, 1995; Merlini et al., 1995, supra). Secondary or reactive amyloidosis is an inflammation-associated disorder in which AA protein is deposited in several organs. The AA protein is a 76 residues N-terminal fragment derived from proteolysis of a precursor called serum amyloid A (SAA) protein (Levin et al., 1972, supra).

Experimental amyloidosis in mice was induced by injection of amyloid enhancing factor (AEF) and silver nitrate. Under these conditions the animals developed amyloid deposits in the spleen after 36–48 h of the injection (Kisilevsky et al., 1983, supra). We examined the effect of iAβ on AA amyloid formation after 5 days. When 5 mg of iAβ were injected together with AEF, after 24 h of preincubation, the area occupied by amyloid in the spleen was decreased in approximately 86.4% in comparison with the animals treated without the inhibitor (Table 2).

TABLE 2

Effect of iAβ on in vivo amyloid deposition using the animal model of amyloid-A amyloidosis. Amyloid was induced by injection of amyloid enhancing factor (AEF) and silver nitrate (SN). Animals were sacrificed at 5 days and amyloid detected immunohistochemically using an antibody to serum amyloid A protein and quantitated by image analysis, as described in Methods.

| Animal | AEF/SN | Control[a] untreated | AEF/SN + iAβ[b] |
|---|---|---|---|
| 1 | 29.4 | 0.05 | 4.35 |
| 2 | 31.65 | 0.1 | 3.68 |
| 3 | 32.97 | 0.21 | 5.32 |
| 4 | 30.77 | 0.04 | 3.67 |
| Average ± SE[c] | 31.2 ± 0.75 | 0.10 ± 0.04 | 4.26 ± 0.39 |

[a]Represents the group of animals not treated with AEF/SN
[b]AEF (100 μg) was preincubated with 5 mg of IBAP1 for 24 h and then injected together into the mice along with SN.
[c]Standard error Effect of iAβ on the promotion of Aβ fibrillogenesis induced by apoliprotein E. It is thought that sAβ in human body fluids is complexed to apolipoproteins, especially apolipoprotein (apo) J and E (Maggio et al., *Proc. Natl. Acad. Sci. USA* 89:5462–5466, 1992). These proteins as well as others (proteoglycans, amyloid P component, α1-antichymotrypsin, etc) are found in senile plaques and congophilic vessels (Tamaoka et al., *biochem. Biophys. Res. Commun.* 205:834–842, 1994). Several of these amyloid-associated proteins bind to Aβ in solution and modulate the rate of amyloid formation in vitro (Moore. G. J. *Trends Pharmacol. Sci.* 15:124–129, 1994; Wisniewski et al., *Am. J. Pathol.* 145:1030–1035, 1994; Ma et al., *Nature* 372:92–94, 1994; Snow et al., *Neuron.* 12:219–234, 1994).

Figure 18:
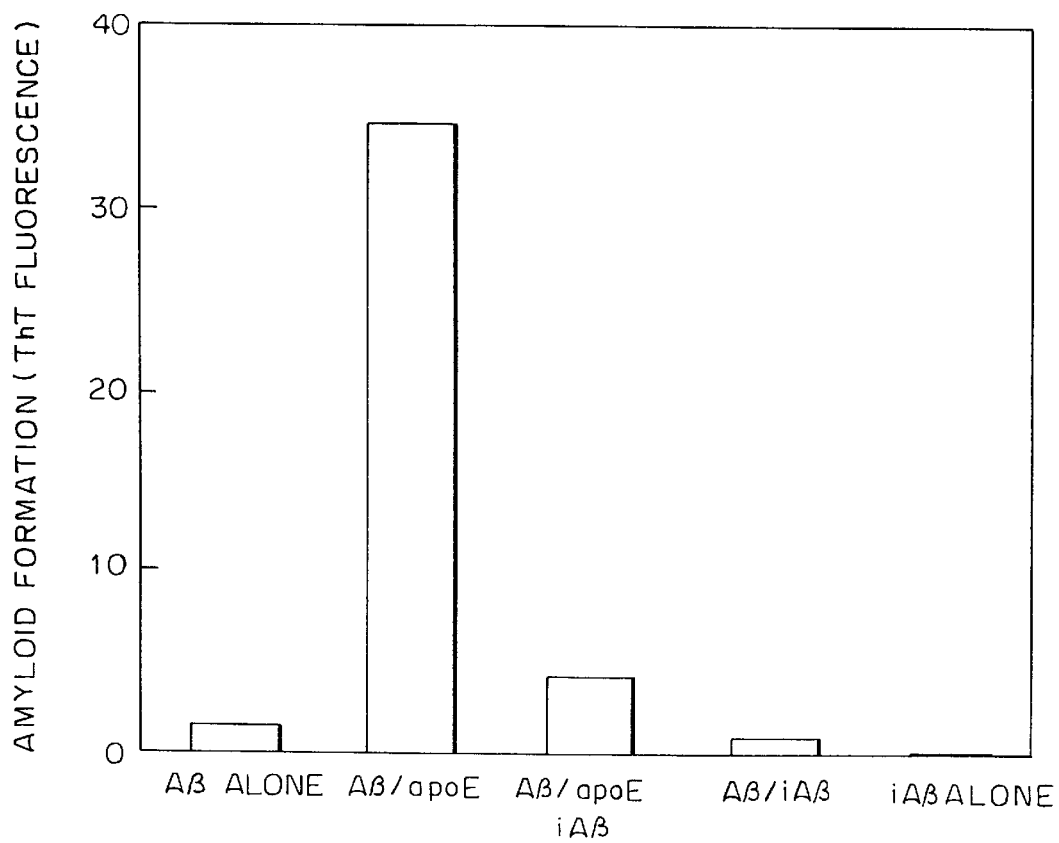
FIG. 18 shows the effect of iAβ on the promotion of Aβ fibrillogenesis induced by apolipoprotein E. 30 μg of Aβ1-40 were incubated with or without 2.4 μg of human plasma apolipoprotein E (apoE). Samples of Aβ alone or Aβ/apoE were incubated also with 1:10 (Aβ:iAβ) of the inhibitor. All the incubators were performed for 24 h at room temperature. Amyloid formation was evaluated by the thioflavine T fluorometric assay. The average of two different experiments is shown.

The results shown in FIG. 18 show that iAβ blocked the promotion of Aβ fibrillogenesis induced by apo E. Preliminary experiments also indicate that heparan-sulfate proteoglucan-induced Aβ fibrillogenesis is blocked as well by iAβ.

Dissolution of Alzheimer's amyloid plaque by iAβ.

Figure 19:
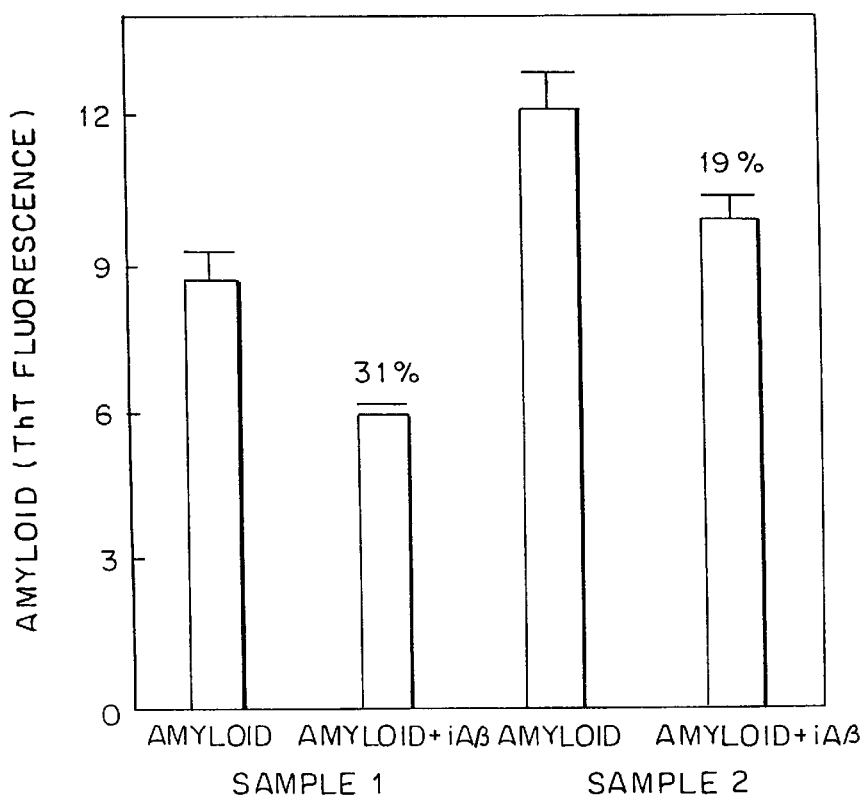
FIG. 19 shows Alzheimer's amyloid plaque dissolution by iAβ.
Figure 20:
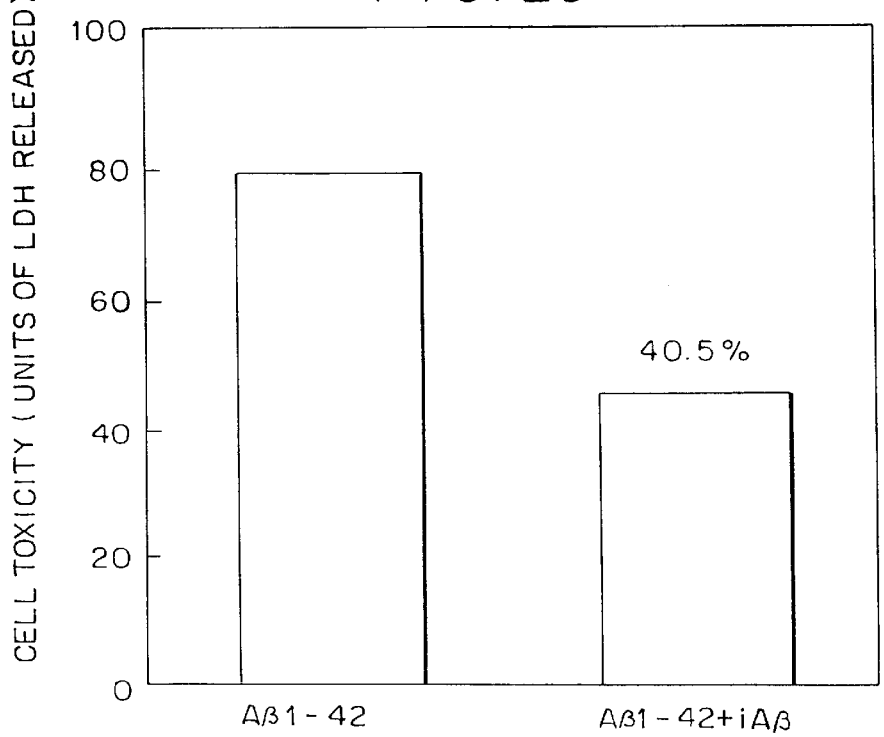
FIG. 20 shows the effect of iAβ on the Aβ-induced cell toxicity.

Amyloid was isolated from mature senile plaque extracted from a brain of a patient who died of Alzheimer's disease. Grey matter was separated from meninges and white matter, cleaned, chopped and homogenized in buffer containing 0.25M sucrose. The homogenate was subjected to a series of centrifugation, treatment with DNase I and collagenase and to a discontinuous sucrose density gradient. After this procedure, pure amyloid cores containing >90% Aβ and also several of the amyloid-associated associated proteins was obtained. 10 μg of amyloid proteins was incubated for 5 days without and with 200 μg of iAβ. The amount of amyloid was quantitated by using the fluorometric assay based in the binding of thioflavine T to amyloid, as described (Soto, C., et al., *J. Biol. Chem.* 270:3063–3067, 1995). The material obtained from two different extractions was tested (Samples 1 and 2) and the average and standard error of three different experiments was shown in FIG. 19.

Effect of iAβ on Aβ-induced cell toxicity.

Neuronal differentiated human neuroblastoma cells (IMR-32) were obtained from American Type Culture Collection and were grown using the standard protocols. Fresh Aβ1-42 was added to the medium to reach a final concentration of 30 μM. The inhibitor (final concentration 600 μM) was added together or preincubated with Aβ1-42 for 24 h. After 48 h cell toxicity was evaluated by using the lactate dehydrogenase (LDH) release assay (Simmons, et al., *Mol. Pharmacol.* 45:373–379, 1994), using a kit obtained from Sigma. The results shown correspond to the average between two different experiments.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for reducing the formation of amyloid or amyloid-like deposits involving the abnormal folding into a β-sheet structure of a protein or peptide having a sequence predicted to adopt a β-sheet structure, or for reducing the amount of said protein or peptide which has already formed into a β-sheet structure, comprising:

bringing into the presence of said protein or peptide, either prior to or after the abnormal folding thereof into a β-sheet structure, an effective amount of an inhibiting peptide comprising a portion of three to eight amino acids, which portion is hydrophobic and has one or more proline residues therein, said inhibitory peptide having a length of three to fifteen amino acids and a sequence predicted not to adopt a β-sheet conformation as calculated by the Chou and Fasman secondary structure prediction algorithm and, when incubated with said protein or peptide, or a portion thereof having a sequence predicted to adopt a β-sheet conformation as calculated by the Chou and Fasman secondary structure prediction algorithm, inhibits the folding thereof into a β-sheet structure.

2. The method in accordance with claim 1, wherein at least some amino acid residues of said inhibitory peptide are D-amino acid residues.

3. The method in accordance with claim 1, wherein said inhibitory peptide further includes one or more charged residues at one or both ends thereof.

4. The method in accordance with claim 1, wherein said protein or peptide having a sequence predicted to adopt a β-sheet structure is amyloid β-peptide.

5. The method in accordance with claim 1, wherein said protein or peptide having a sequence predicted to adopt a β-sheet structure is prion PrP protein.

6. The method in accordance with claim 1, wherein said inhibitory peptide has a sequence selected from the group consisting of SEQ ID NOs:7, 8, 9, 10, 15, 16, 17, 18, 19, 20, 21, 22, 24, 25, and Pro-Phe-Phe.

7. The method in accordance with claim 6, wherein said inhibitory peptide has the sequence of SEQ ID NO:8.

8. A method for reducing the formation of amyloid or amyloid-like deposits involving the abnormal folding into a β-sheet structure of a protein or peptide having a sequence predicted to adopt a β-sheet structure, or for reducing the amount of said protein or peptide which has already formed into a β-sheet structure, comprising:

bringing into the presence of said protein or peptide, either prior to or after the abnormal folding thereof into a β-sheet structure, an effective amount of an inhibitory peptide having a length of three to fifteen amino acids and comprising a portion of three to eight amino acids, which portion is hydrophobic and has one or more β-sheet blocking amino acid residues therein, said inhibitory peptide being one which has a circular dichroism spectrum in aqueous solution typical of unordered structures, which does not aggregate at a concentration of 4 mg/ml, and which, when incubated with said protein or peptide, or a portion thereof having a sequence predicted to adopt a β-sheet structure as calculated by the Chou and Fasman secondary structure prediction algorithm, inhibits the folding thereof into a β-sheet structure.

9. A method in accordance with claim 8, wherein said inhibitory peptide further includes one or more charged residues at one or both ends thereof.

10. The method in accordance with claim 8, wherein at least some amino acid residues of said inhibitory peptide are D-amino acid residues.

11. The method in accordance with claim 8, wherein said protein or peptide having a sequence predicted to adopt a β-sheet structure is amyloid β-peptide.

12. The method in accordance with claim 8, wherein said protein or peptide having a sequence predicted to adopt a β-sheet structure is prion PrP protein.

13. The method in accordance with claim 8, wherein said inhibitory peptide has a sequence selected from the group consisting of SEQ ID NOs:7, 8, 9, 10, 15, 16, 17, 18, 19, 20, 21, 22, 24, 25, and Pro-Phe-Phe.

14. A method in accordance with claim 13, wherein said inhibitory peptide has the sequence of SEQ ID NO:8.

* * * * *